(12) United States Patent
Bonnette et al.

(10) Patent No.: US 11,464,941 B2
(45) Date of Patent: Oct. 11, 2022

(54) DIRECT STREAM HYDRODYNAMIC CATHETER SYSTEM

(71) Applicant: BOSTON SCIENTIFIC LIMITED, Hamilton (BM)

(72) Inventors: Michael J. Bonnette, Minneapolis, MN (US); Eric J. Thor, Arden Hills, MN (US); Debra M. Kozak, Forest Lake, MN (US); Douglas J. Ball, Blaine, MN (US); Stephen E. Weisel, Brook Park, MN (US); David B. Morris, Anoka, MN (US); Richard R. Prather, St. Michael, MN (US)

(73) Assignee: Boston Scientific Limited, Hamilton (BM)

( * ) Notice: Subject to any disclaimer, the term of this patent is extended or adjusted under 35 U.S.C. 154(b) by 519 days.

(21) Appl. No.: 16/440,949

(22) Filed: Jun. 13, 2019

(65) Prior Publication Data
US 2019/0290315 A1    Sep. 26, 2019

Related U.S. Application Data

(60) Continuation of application No. 15/452,328, filed on Mar. 7, 2017, now Pat. No. 10,321,932, which is a
(Continued)

(51) Int. Cl.
*A61M 25/00* (2006.01)
*A61B 17/3203* (2006.01)
(Continued)

(52) U.S. Cl.
CPC ... *A61M 25/0068* (2013.01); *A61B 17/32037* (2013.01); *A61M 25/007* (2013.01);
(Continued)

(58) Field of Classification Search
CPC ........ A61B 17/32037; A61B 2217/007; A61B 2017/22068; A61B 2017/22079;
(Continued)

(56) References Cited

U.S. PATENT DOCUMENTS

| 1,902,418 A | 3/1933 | Pilgrim |
| 3,435,826 A | 4/1969 | Fogarty |

(Continued)

FOREIGN PATENT DOCUMENTS

| DE | 3421390 C2 | 7/1986 |
| DE | 3705339 A1 | 9/1988 |

(Continued)

OTHER PUBLICATIONS

European Search Report dated Jun. 1, 1999 from European Application No. 99300846.
(Continued)

*Primary Examiner* — Lauren P Farrar
(74) *Attorney, Agent, or Firm* — Seager, Tufte & Wickhem LLP

(57) ABSTRACT

A direct stream hydrodynamic catheter system is provided for the removal of thrombus, lesions and the like including provisions for the infusion of drugs, lysing fluids and the like into a blood vessel. Physician controlled powered direct fluid jet streams emanate from a fluid jet emanatory in the form of robust radially directed fluid jet streams to impinge upon and ablate difficult and strong thrombus and lesions within a blood vessel. Effluent aspiration is controlled by an exhaust regulator in the form of a roller pump, but effluent removal can be assistingly influenced by the fluid pressure associated with the radially directed fluid jet streams.

17 Claims, 26 Drawing Sheets

Related U.S. Application Data division of application No. 14/176,814, filed on Feb. 10, 2014, now Pat. No. 9,586,023, which is a division of application No. 12/933,520, filed as application No. PCT/US2009/037814 on Mar. 20, 2009, now Pat. No. 8,647,294.

(60) Provisional application No. 61/070,095, filed on Mar. 20, 2008.

(51) Int. Cl.
*A61M 25/10* (2013.01)
*A61B 17/22* (2006.01)

(52) U.S. Cl.
CPC .......... *A61M 25/0026* (2013.01); *A61B 2017/22068* (2013.01); *A61B 2017/22079* (2013.01); *A61B 2217/005* (2013.01); *A61B 2217/007* (2013.01); *A61M 25/10* (2013.01); *A61M 2025/0004* (2013.01); *A61M 2025/0073* (2013.01)

(58) Field of Classification Search
CPC ........ A61B 2217/005; A61M 25/0026; A61M 25/007; A61M 25/0068; A61M 2025/0073; A61M 2025/0004; A61M 25/10
See application file for complete search history.

(56) References Cited

U.S. PATENT DOCUMENTS

| | | |
|---|---|---|
| 3,695,208 A | 10/1972 | Fixler |
| 3,752,617 A | 8/1973 | Burlis et al. |
| 3,833,003 A | 9/1974 | Taricco |
| 3,930,505 A | 1/1976 | Wallach |
| 4,100,246 A | 7/1978 | Frisch |
| 4,168,709 A | 9/1979 | Bentov |
| 4,224,943 A | 9/1980 | Johnson et al. |
| 4,248,234 A | 2/1981 | Assenza et al. |
| 4,290,428 A | 9/1981 | Durand et al. |
| 4,328,811 A | 5/1982 | Fogarty |
| 4,385,635 A | 5/1983 | Ruiz |
| 4,515,592 A | 5/1985 | Frankhouser |
| 4,535,757 A | 8/1985 | Webster, Jr. |
| 4,610,662 A | 9/1986 | Weikl et al. |
| 4,631,052 A | 12/1986 | Kensey |
| 4,636,346 A | 1/1987 | Gold et al. |
| 4,690,672 A | 9/1987 | Veltrup |
| 4,739,768 A | 4/1988 | Engelson |
| 4,747,405 A | 5/1988 | Leckrone |
| 4,781,186 A | 11/1988 | Simpson et al. |
| 4,782,834 A | 11/1988 | Maguire et al. |
| 4,790,813 A | 12/1988 | Kensey |
| 4,834,710 A | 5/1989 | Fleck |
| 4,842,579 A | 6/1989 | Shiber |
| 4,883,459 A | 11/1989 | Calderon |
| 4,888,146 A | 12/1989 | Dandeneau |
| 4,898,574 A | 2/1990 | Uchiyama et al. |
| 4,898,591 A | 2/1990 | Jang et al. |
| 4,902,276 A | 2/1990 | Zakko |
| 4,913,698 A | 4/1990 | Ito et al. |
| 4,917,667 A | 4/1990 | Jackson |
| 4,950,238 A | 8/1990 | Sullivan |
| 5,011,469 A | 4/1991 | Buckberg et al. |
| 5,015,232 A | 5/1991 | Maglinte |
| 5,042,976 A | 8/1991 | Ishitsu et al. |
| 5,085,549 A | 2/1992 | Londry |
| 5,085,635 A | 2/1992 | Cragg |
| 5,085,649 A | 2/1992 | Flynn |
| 5,086,842 A | 2/1992 | Cholet |
| 5,090,960 A | 2/1992 | Don Michael |
| 5,092,873 A | 3/1992 | Simpson et al. |
| 5,114,399 A | 5/1992 | Kovalcheck |
| 5,135,482 A | 8/1992 | Neracher |
| 5,163,431 A | 11/1992 | Griep |
| 5,171,221 A | 12/1992 | Samson |
| 5,215,614 A | 6/1993 | Wijkamp et al. |
| 5,221,270 A | 6/1993 | Parker |
| 5,222,941 A | 6/1993 | Don Michael |
| 5,234,416 A | 8/1993 | Macaulay et al. |
| 5,242,395 A | 9/1993 | Maglinte |
| 5,250,034 A | 10/1993 | Appling et al. |
| 5,250,059 A | 10/1993 | Andreas et al. |
| 5,254,107 A | 10/1993 | Soltesz |
| 5,259,842 A | 11/1993 | Plechinger et al. |
| 5,267,979 A | 12/1993 | Appling et al. |
| 5,273,526 A | 12/1993 | Dance et al. |
| 5,300,022 A | 4/1994 | Klapper et al. |
| 5,306,249 A | 4/1994 | Don Michel |
| 5,308,342 A | 5/1994 | Sepetka et al. |
| RE34,633 E | 6/1994 | Sos et al. |
| 5,318,518 A | 6/1994 | Plechinger et al. |
| 5,320,599 A | 6/1994 | Griep et al. |
| 5,324,285 A | 6/1994 | Cannon |
| 5,331,679 A | 7/1994 | Hirukawa |
| 5,342,386 A | 8/1994 | Trotta |
| 5,356,388 A | 10/1994 | Sepetka et al. |
| 5,358,485 A | 10/1994 | Vance et al. |
| 5,360,379 A | 11/1994 | Carelli et al. |
| 5,360,397 A | 11/1994 | Pinchuk |
| 5,370,609 A | 12/1994 | Drasler et al. |
| 5,372,601 A | 12/1994 | Lary |
| 5,380,307 A | 1/1995 | Chee et al. |
| 5,385,548 A | 1/1995 | Williams et al. |
| 5,395,315 A | 3/1995 | Griep |
| 5,399,164 A | 3/1995 | Snoke et al. |
| 5,409,454 A | 4/1995 | Fischell et al. |
| 5,425,723 A | 6/1995 | Wang |
| 5,456,665 A | 10/1995 | Postell et al. |
| 5,456,674 A | 10/1995 | Bos et al. |
| 5,478,330 A | 12/1995 | Imran et al. |
| 5,492,532 A | 2/1996 | Ryan et al. |
| 5,496,267 A | 3/1996 | Drasler et al. |
| 5,496,294 A | 3/1996 | Hergenrother et al. |
| 5,499,973 A | 3/1996 | Saab |
| 5,513,956 A | 5/1996 | Lewis et al. |
| 5,514,092 A | 5/1996 | Forman et al. |
| 5,531,679 A | 7/1996 | Schulman et al. |
| 5,531,685 A | 7/1996 | Hemmer et al. |
| 5,536,242 A | 7/1996 | Willard et al. |
| 5,542,924 A | 8/1996 | Snoke et al. |
| 5,554,121 A | 9/1996 | Ainsworth et al. |
| 5,558,642 A | 9/1996 | Schweich, Jr. et al. |
| 5,571,094 A | 11/1996 | Sirhan |
| 5,599,299 A | 2/1997 | Weaver et al. |
| 5,599,325 A | 2/1997 | Ju et al. |
| 5,609,574 A | 3/1997 | Kaplan et al. |
| 5,624,397 A | 4/1997 | Snoke et al. |
| 5,628,730 A | 5/1997 | Shapland et al. |
| 5,634,897 A | 6/1997 | Dance et al. |
| 5,643,279 A | 7/1997 | Trotta |
| 5,658,263 A | 8/1997 | Dang et al. |
| 5,662,608 A | 9/1997 | Imran et al. |
| 5,662,622 A | 9/1997 | Gore et al. |
| 5,668,702 A | 9/1997 | Nassimi |
| 5,676,659 A | 10/1997 | McGurk |
| 5,681,336 A | 10/1997 | Clement et al. |
| 5,683,345 A | 11/1997 | Waksman et al. |
| 5,687,714 A | 11/1997 | Kolobow et al. |
| 5,702,439 A | 12/1997 | Keith et al. |
| 5,704,926 A | 1/1998 | Sutton |
| 5,713,849 A | 2/1998 | Bosma et al. |
| 5,769,828 A | 6/1998 | Jonkman |
| 5,792,167 A | 8/1998 | Kablik et al. |
| 5,795,322 A | 8/1998 | Boudewijn |
| 5,795,325 A | 8/1998 | Valley et al. |
| 5,817,046 A | 10/1998 | Glickman |
| 5,843,022 A | 12/1998 | Willard et al. |
| 5,906,590 A | 5/1999 | Hunjan et al. |
| 5,919,163 A | 7/1999 | Glickman |
| 5,928,181 A | 7/1999 | Coleman et al. |
| 5,929,633 A | 7/1999 | Fischer |

(56) References Cited

U.S. PATENT DOCUMENTS

| | | | |
|---|---|---|---|
| 5,935,501 A | 8/1999 | Andrews et al. |
| 5,939,320 A | 8/1999 | Littman et al. |
| 5,944,686 A | 8/1999 | Patterson et al. |
| 5,951,513 A | 9/1999 | Miraki |
| 5,957,901 A | 9/1999 | Mottola et al. |
| 5,989,210 A | 11/1999 | Morris et al. |
| 5,989,271 A | 11/1999 | Bonnette et al. |
| 6,001,078 A | 12/1999 | Reekers |
| 6,004,269 A | 12/1999 | Crowley et al. |
| 6,004,339 A | 12/1999 | Wijay |
| 6,022,336 A | 2/2000 | Zadno-Azizi et al. |
| 6,024,729 A | 2/2000 | Dehdashtian et al. |
| 6,027,499 A | 2/2000 | Johnston et al. |
| 6,044,845 A | 4/2000 | Lewis |
| 6,062,623 A | 5/2000 | Lemmen |
| 6,063,069 A | 5/2000 | Cragg et al. |
| 6,068,623 A | 5/2000 | Zadno-Azizi et al. |
| 6,074,374 A | 6/2000 | Fulton |
| 6,096,001 A | 8/2000 | Drasler et al. |
| 6,099,496 A | 8/2000 | Berthiaume et al. |
| 6,106,642 A | 8/2000 | DiCarlo et al. |
| 6,129,697 A | 10/2000 | Drasler et al. |
| 6,129,698 A | 10/2000 | Beck |
| 6,135,977 A | 10/2000 | Drasler et al. |
| 6,165,199 A | 12/2000 | Barbut |
| 6,179,816 B1 | 1/2001 | Mottola et al. |
| RE37,153 E | 5/2001 | Henszey et al. |
| 6,224,570 B1 | 5/2001 | Le et al. |
| 6,241,744 B1 | 6/2001 | Imran et al. |
| 6,258,061 B1 | 7/2001 | Drasler et al. |
| 6,273,880 B1 | 8/2001 | Berg et al. |
| 6,283,950 B1 | 9/2001 | Appling |
| 6,331,176 B1 | 12/2001 | Becker et al. |
| 6,375,635 B1 | 4/2002 | Moutafis et al. |
| 6,524,300 B2 | 2/2003 | Meglin |
| 6,533,782 B2 | 3/2003 | Howell et al. |
| 6,544,220 B2 | 4/2003 | Shuman et al. |
| 6,592,549 B2 | 7/2003 | Gerdts et al. |
| 6,652,548 B2 | 11/2003 | Evans et al. |
| 6,656,550 B1 | 12/2003 | Zamore |
| 6,676,637 B1 | 1/2004 | Bonnette et al. |
| 6,749,583 B2 | 6/2004 | Briscoe et al. |
| 6,755,803 B1* | 6/2004 | Le .................. A61B 17/32037 604/22 |
| 6,773,452 B2 | 8/2004 | Shaker |
| 6,805,692 B2 | 10/2004 | Muni et al. |
| 6,834,842 B2 | 12/2004 | Houde |
| 6,875,193 B1 | 4/2005 | Bonnette et al. |
| 6,926,726 B2 | 8/2005 | Drasler et al. |
| 6,929,633 B2 | 8/2005 | Evans et al. |
| 6,939,320 B2 | 9/2005 | Lennox |
| 6,942,635 B2 | 9/2005 | Rosenblatt et al. |
| 6,945,951 B1 | 9/2005 | Bonnette et al. |
| 7,033,776 B2 | 4/2006 | Toombs |
| 7,131,981 B2 | 11/2006 | Appling et al. |
| 7,163,533 B2 | 1/2007 | Hobbs et al. |
| 7,182,756 B2 | 2/2007 | Saeed et al. |
| 7,220,269 B1 | 5/2007 | Ansel et al. |
| 7,226,433 B2 | 6/2007 | Bonnette et al. |
| 7,314,461 B2 | 1/2008 | Carter et al. |
| 7,369,358 B2 | 5/2008 | Edelman et al. |
| 7,374,560 B2 | 5/2008 | Ressemann et al. |
| 7,396,358 B2 | 7/2008 | Appling et al. |
| 7,399,307 B2 | 7/2008 | Evans et al. |
| 7,422,579 B2 | 9/2008 | Wahr et al. |
| 7,500,982 B2 | 3/2009 | Pepper |
| 7,726,433 B2 | 6/2010 | Satou et al. |
| 7,879,022 B2 | 2/2011 | Bonnette et al. |
| 2001/0051785 A1 | 12/2001 | Bonnette et al. |
| 2001/0051811 A1 | 12/2001 | Bonnette et al. |
| 2001/0053920 A1 | 12/2001 | Shaker |
| 2001/0056257 A1 | 12/2001 | Drasler et al. |
| 2002/0032408 A1 | 3/2002 | Parker et al. |
| 2002/0049423 A1 | 4/2002 | Howell et al. |
| 2002/0068895 A1 | 6/2002 | Beck |
| 2002/0077594 A1 | 6/2002 | Chien et al. |
| 2002/0120226 A1 | 8/2002 | Beck |
| 2002/0188276 A1 | 12/2002 | Evans et al. |
| 2003/0069541 A1 | 4/2003 | Gillis et al. |
| 2003/0088194 A1 | 5/2003 | Bonnette et al. |
| 2003/0139751 A1 | 7/2003 | Evans et al. |
| 2003/0195490 A1 | 10/2003 | Boatman et al. |
| 2004/0006306 A1 | 1/2004 | Evans et al. |
| 2004/0019323 A1 | 1/2004 | Carter et al. |
| 2004/0039306 A1 | 2/2004 | Eberhart et al. |
| 2004/0068248 A1 | 4/2004 | Mooney |
| 2004/0093008 A1 | 5/2004 | Zamore |
| 2004/0193196 A1 | 9/2004 | Appling et al. |
| 2004/0210194 A1 | 10/2004 | Bonnette et al. |
| 2005/0049574 A1 | 3/2005 | Petrick et al. |
| 2005/0059957 A1 | 3/2005 | Campbell et al. |
| 2005/0107738 A1 | 5/2005 | Slater et al. |
| 2005/0215989 A1* | 9/2005 | Abboud .......... A61M 25/10185 606/41 |
| 2006/0016064 A1 | 1/2006 | Boatman et al. |
| 2006/0047239 A1 | 3/2006 | Nita et al. |
| 2006/0054123 A1 | 3/2006 | Stein et al. |
| 2006/0064123 A1 | 3/2006 | Bonnette et al. |
| 2006/0129091 A1 | 6/2006 | Bonnette et al. |
| 2006/0217791 A1 | 9/2006 | Spinka et al. |
| 2006/0229645 A1 | 10/2006 | Bonnette et al. |
| 2007/0010847 A1 | 1/2007 | Pepper |
| 2007/0073233 A1 | 3/2007 | Thor et al. |
| 2007/0282303 A1 | 12/2007 | Nash et al. |
| 2007/0282422 A1 | 12/2007 | Biggs et al. |
| 2008/0033350 A1 | 2/2008 | Wilson et al. |
| 2008/0188830 A1 | 8/2008 | Rosenblatt et al. |
| 2008/0275393 A1 | 11/2008 | Bonnette et al. |
| 2008/0300576 A1 | 12/2008 | Vitullo et al. |
| 2008/0306427 A1 | 12/2008 | Bailey |
| 2008/0312672 A1 | 12/2008 | Bonnette et al. |

FOREIGN PATENT DOCUMENTS

| | | |
|---|---|---|
| EP | 0232678 B1 | 4/1991 |
| EP | 0251512 B1 | 8/1994 |
| EP | 0528181 B1 | 10/1997 |
| EP | 1382366 A1 | 1/2004 |
| GB | 1571459 A | 7/1980 |
| WO | 9005493 A1 | 5/1990 |
| WO | 9410917 A1 | 5/1994 |
| WO | 9510232 A1 | 4/1995 |
| WO | 2007067661 A2 | 6/2007 |

OTHER PUBLICATIONS

International Search Report dated Sep. 13, 2007 from International Application No. PCT/US2005/041412.

FrontRunnerXP CTO Catheter Technical Sheet, Lumend Inc., www.medcompare.com/details/6709/Frontrunner-XP-CTO-Catheter.html, 2 pages, Feb. 8, 2010.

Outback LTD Re-Entry Catheter Technical Sheet, accessed at http://www.cordis.com/emea/il/product/outback-ltd-re-entry-catheter, accessed on Apr. 14, 2014, pp. 1-2.

Delrin Acetal Resin, DePont, accessed at http://www.dupont.co.in/products-and-services/plastics-polymers-resins/thermoplastics/brands/delrin-acetal-resin.html, accessed on Feb. 8, 2010.

International Search Report dated Oct. 2, 2008 from International Application No. PCT/US2008/065736.

International Preliminary Report on Patentability dated Dec. 17, 2009 from International Application No. PCT/US2008/065736.

International Preliminary Report on Patentability dated Dec. 22, 2009 from International Application No. PCT/US2008/066039.

International Search Report dated Feb. 12, 2009 from International Application No. PCT/US2008/087422.

International Search Report dated Feb. 11, 2009 from International Application No. PCT/US2008/087109.

International Search Report dated Nov. 10, 2008 from International Application No. PCT/US2006/046621.

Trellis Peripheral Infusion System, Bacchus Vascular, Inc. website, Nov. 20, 2008.

(56) References Cited

OTHER PUBLICATIONS

International Search Report dated Mar. 29, 2006 from International Application No. PCT/US2005/014644.
International Preliminary Report on Patentability dated Sep. 21, 2010 from International Application No. PCT/US2009/037814.
International Search Report dated Oct. 2, 2008 from International Application No. PCT/US08/66039.
ClearWay RX Product Brochure, corporate website (www.atrimmed.com), Atrium Medical Corporation, as early as Oct. 2007.
Safe-Cross RF CTO System Technical Sheet, Kensey Nash, www.kenseynash.com, 5 pages, Feb. 9, 2011.
"Bracchus Vascular, Inc. Release: Trellis(R) Peripheral Infusion System Removes Blood Clots in Largest Reported Prospective Endovascular DVT (Deep Vein Thrombosis) Patient," BioSpace, accessed at https://www.biospace.com/News/bacchus-vascular-inc-release-trellisr-peripheral/118262, Nov. 20, 2008, pp. 1-2.

* cited by examiner

DIRECT STREAM HYDRODYNAMIC CATHETER SYSTEM

CROSS REFERENCES TO RELATED APPLICATIONS

This application is a continuation of U.S. patent application Ser. No. 15/452,328, filed Mar. 7, 2017, now U.S. Pat. No. 10,321,932; which is a divisional of U.S. patent application Ser. No. 14/176,814, filed Feb. 10, 2014, now U.S. Pat. No. 9,586,023; which is a divisional of U.S. patent application Ser. No. 12/933,520, filed Sep. 20, 2010, now U.S. Pat. No. 8,647,294, which is a 371 Application of PCT/US2009/037814, filed Mar. 20, 2009, which claims the benefit of U.S. Provisional Patent Application No. 61/070,095, filed Mar. 20, 2008, entitled "Direct Spray Disruption and Removal Catheter", the entire disclosures of which are incorporated herein by reference.

This patent application is related to U.S. patent application Ser. No. 10/455,096 filed Jun. 5, 2003, entitled "Thrombectomy Catheter Device Having a Self-Sealing Hemostasis Valve", now U.S. Pat. No. 7,226,433, which is a Continuation-In-Part (CIP) of application Ser. No. 10/198,264 filed Jul. 16, 2002, entitled "Rapid Exchange Fluid Jet Thrombectomy Device and Method", now U.S. Pat. No. 6,875,193, which is a Continuation-In-Part (CIP) of application Ser. No. 09/888,455 filed Jun. 25, 2001, now U.S. Pat. No. 6,755,803, which is a Continuation-In-Part (CIP) of application Ser. No. 09/356,783 filed Jul. 16, 1999, now abandoned, which is a divisional of application Ser. No. 09/019,728 filed Feb. 6, 1998, now U.S. Pat. No. 5,989,210, and are hereby incorporated into this application by reference as if fully set forth herein.

This patent application is also related to application Ser. No. 11/096,592 filed Apr. 1, 2005, entitled "Rapid Exchange Fluid Jet Thrombectomy Device and Method", which is now U.S. Pat. No. 7,879,022, and which is a Continuation-In-Part (CIP) of application Ser. No. 10/198,264 filed Jul. 16, 2002, entitled "Rapid Exchange Fluid Jet Thrombectomy Device and Method", now U.S. Pat. No. 6,875,193, which is a Continuation-In-Part (CIP) of application Ser. No. 09/888,455 filed Jun. 25, 2001, now U.S. Pat. No. 6,755,803, which is a Continuation-In-Part (CIP) of application Ser. No. 09/356,783 filed Jul. 16, 1999, now abandoned, which is a divisional of application Ser. No. 09/019,728 filed Feb. 6, 1998, now U.S. Pat. No. 5,989,210, and are hereby incorporated into this application by reference as if fully set forth herein.

BACKGROUND OF THE INVENTION

1. Field of the Invention

The general purpose of this disclosure is to provide a direct stream hydrodynamic catheter system for use in thrombectomies and associated procedures. More specifically is disclosed a direct stream hydrodynamic catheter system, preferably in the form of radially directed fluid jet streams, which uses controlled fluid jet streams to accomplish a thrombectomy of highly organized material or to accomplish infusion of drugs to a conduit wall, or as shown in alternative embodiments, to accomplish cell sampling of the conduit wall. The device is primarily intended for use as an enhanced thrombectomy device which can be beneficial for robust and aggressive removal of thrombus, lesions and the like from coronary arteries, peripheral arteries or veins, neurological arteries or veins, or arterial venous conduits.

2. Description of the Prior Art

Prior art thrombectomy devices provide structures for the removal of thrombus, lesions, gummous material and the like from the vasculature, but do little to address the control of fluid jet streams which are instrumental in accomplishing interventional procedures. Some prior art thrombectomy devices use indirect cross path fluid jet streams, the axial path of which can be diminished and of insufficient strength which do not utilize full strength, such as provided by the radially directed fluid jet streams disclosed here. Fluid jet streams produced by prior art devices, if not controlled effectively, may not accomplish a thrombectomy in a satisfactory manner or may cause undesirable damage. If the strength of the fluid jet streams is excessive, damage may occur to a blood vessel wall, and if the strength of the fluid jet stream is insufficient, then a satisfactory thrombectomy may not be accomplished. As presented in this disclosure, consideration is given to provide a catheter system for an aggressive and robust thrombectomy by controlling the volumetric flow rate which can be influenced by its structure and which may be controlled by a physician in its use.

SUMMARY OF THE INVENTION

The general purpose of this disclosure is to provide a direct stream hydrodynamic catheter system also referred to herein as the catheter system. This disclosure describes the use of a direct spray in the form of radially directed fluid jet streams emanating from an emanator at the distal end of a direct stream hydrodynamic catheter tube, synonymously referred to as a catheter tube, for purposes of, but not limited to, a thrombectomy of a highly organized material or the infusion of drugs into a vascular conduit. The direct stream hydrodynamic catheter system provides for a physician controlling a high pressure fluid pump and a high pressure fluid source for the purposes of delivering pressurized saline with or without medicaments to an emanator at the distal end of a catheter tube tip in order to provide for the emanation of radially directed fluid jet streams and to provide for a hydrodynamic action in the direct impingement of deposits in the vascular conduit. An inflow orifice is included near the distal end of the catheter tube proximal to a fluid jet emanator to receive freed thrombus or lesion particles which are evacuated through the catheter tube. There is also a collection chamber and an exhaust regulator in the form of a roller pump which can be operated by a physician and which is used to provide for the evacuation and control of the evacuation rate, i.e., aspiration of the catheter tube. The present disclosure provides for the structure of and use of a catheter tube whereby fluid jet streams are directed radially and outwardly from a fluid jet emanator or optionally at any other beneficial angle in a distal or proximal direction in order to directly impinge upon the vascular conduit unimpeded by any device structure. The inflow orifice is provided proximal to the fluid jet emanator to provide for the ingestion and entrainment of thrombus or lesion particles which are freed from the interior of the vasculature by radially directed fluid jet streams. The exhaust roller pump can be operated by a physician to control the rate to aspirate liberated thrombus or lesions or can be used, such as shown in an alternative embodiment, to assist in the aspiration of conduit wall cell samples.

The desired velocity and strength of the radially directed fluid jet streams can be controlled by using the fluid jet emanator in the distal end of the catheter tube which jet emanator has suitably sized radially directed jet orifices and by using the exhaust regulator for aspiration in coordination with the manipulation of the high pressure fluid pump to produce a desired operating pressure, volume and outflow. As disclosed herein, the catheter system is more robust and aggressive than traditional thrombectomy catheters and preferably is used in situations and in vessel segments which can tolerate aggressive direct stream hydrodynamic action. Another application of the disclosed catheter system is the treatment of venous valves which when embedded in an organized thrombus will lose their function. The devices of the present disclosure are intended to free these venous valves of adherent thrombus by using the radially directed fluid jet streams in order to prevent post phlebitic (post thrombotic) syndrome. Another application is to provide for a more robust thrombectomy of adherent and organized mural thrombus. The devices of the present disclosure can also use the strong radially directed jet streams to drive drugs into the vessel wall.

The preferred embodiment includes the use of nominal size high powered radially directed fluid jet streams emanating from a fluid jet emanator for the ablation of thrombus and lesions and uses aspiration to provide for an effluent flow.

A first alternative embodiment includes the use of nominal sized and high powered radially directed fluid jet streams emanating from a fluid jet emanator and the use of a proximally located balloon which is used to center the distal end of the catheter tube. Proximally directed fluid jet streams emanating from a fluid jet emanator are used to complement the evacuation of effluent flow and to complement the inflation of the proximally located balloon.

A second alternative embodiment includes the use of small sized high powered radially directed fluid jet streams emanating from a fluid jet emanator and also includes proximally directed fluid jet streams emanating from a fluid jet emanator which jet streams are used to complement the aspiration of effluent through the catheter tube.

A third alternative embodiment which can be used for cell harvesting includes the use of small sized high powered radially directed fluid jet streams emanating from a fluid jet emanator and also includes a distally located balloon which is used to center the distal end of the catheter tube. Distally directed fluid jet streams emanating from a fluid jet emanator are used to fill the distally located balloon. Proximally directed fluid jet streams emanating from a fluid jet emanator are optionally used to complement the aspiration of effluent flow.

A fourth alternative embodiment includes the use of distally directed fluid jet streams which emanate from the distally directed jet orifices of a fluid jet emanator and thence through one or more distally located small sized outflow orifices in the distal end of the catheter tube as low power cross stream jets used for thrombus ablation. Proximally directed fluid jet streams emanating from a fluid jet emanator are used to complement the aspiration of effluent through the catheter tube.

A fifth alternative embodiment provides for the use of nominally sized and high powered distally directed fluid jet streams emanating from a fluid jet emanator and proximally directed fluid jet streams emanating from a fluid jet emanator which complement the aspiration of effluent through the catheter tube.

According to an embodiment of the disclosure, there is provided a direct stream hydrodynamic catheter system for the removal of thrombus, lesions and the like including provisions for the infusion of drugs, lysing fluids and the like into the vasculature. A catheter tube having a coaxial high pressure tube and a coaxial distally positioned fluid jet emanator is provided for invasive use and treatment within the vasculature. The proximal end of the catheter tube including the high pressure tube is connected to and aligned within the distal end of a centrally located manifold. The manifold and other connected enabling components include, but are not limited to, a physician controlled high pressure pump and high pressure fluid source, a physician controlled exhaust regulator and a collection chamber provided for the operation of the catheter tube system, a high pressure tube and a fluid jet emanator provided for the emanation of radially directed fluid jet streams to accomplish the loosening and evacuation of loosened thrombus, lesions and fluid from within the vasculature or for dispensing of lysing agents or drugs into the vasculature.

One significant aspect and feature of devices of the present disclosure is the use of radially directed fluid jet streams for the purpose of enhanced thrombectomy of mural thrombus.

Another significant aspect and feature of devices of the present disclosure is the use of direct fluid jet streams which can operate in any desired direction and in multiple arrays, i.e., different points of emanation which can then also operate in any desired direction.

Another significant aspect and feature of devices of the present disclosure is the use of proximally directed fluid jet streams with radially directed fluid jet streams for the purpose of debris maceration along with a power provision.

Another significant aspect and feature of devices of the present disclosure is the use of radially directed fluid jet streams for the purpose of cell sampling.

Another significant aspect and feature of devices of the present disclosure is the use of direct fluid jet streams that have velocities which do not cause hemolysis.

Another significant aspect and feature of devices of the present disclosure is the use of fluid jet streams having enough momentum that can be delivered by a large non-hemolysing fluid jet stream which is equivalent in energy, via an increased flow rate, to a high velocity smaller fluid jet stream.

Yet another significant aspect and feature of devices of the present disclosure is the use of direct radially directed fluid jet streams which are physician controlled by a means of high pressure fuel pump.

Yet another significant aspect and feature of devices of the present disclosure is a direct fluid jet stream disruption, i.e., the erosion, breakup and reduction of thrombus or unwanted cellular matter into particulate by fluid jet streams of saline where effluent consisting of thrombus, and/or cellular particulate, and fluid saline is enhanced and driven, evacuated and removed by aspiration using a physician controlled exhaust regulator in the form of a roller pump.

Another significant aspect and feature of devices of the present disclosure is a direct fluid jet stream disruption, i.e., the erosion, breakup and reduction of thrombus or unwanted cellular matter into particulate by fluid jet streams of saline whereby the effluent consisting of thrombus and/or cellular particulate and the fluid saline is enhanced and driven, evacuated and removed by the use of directed fluid jet streams.

Another significant aspect and feature of devices of the present disclosure is a direct fluid jet stream disruption, i.e., the erosion, breakup and reduction of thrombus or unwanted cellular matter into particulate by fluid jet streams of saline whereby the effluent consisting of thrombus and/or cellular particulate and the fluid saline is enhanced and driven, evacuated and removed by manual aspiration using a syringe.

Another significant aspect and feature of devices of the present disclosure is a direct fluid jet stream disruption, i.e., the erosion, breakup and reduction of thrombus or unwanted cellular matter into particulate by fluid jet streams of saline whereby the effluent consisting of thrombus and/or cellular particulate and the fluid saline is enhanced and driven, evacuated and removed, and whereby the vacuum associated with devices of the present disclosure is controlled by varying the relationship between the inputted fluid jet stream pressure and an exhaust regulator, e.g., a bottled vacuum.

Another significant aspect and feature of devices of the present disclosure is the use of proximal or distal balloons inflated by proximally or distally directed fluid jet streams, respectively, for the purpose of centering the distal portion including the inflow orifice(s) of a catheter tube.

Another significant aspect and feature of devices of the present disclosure is the use of a cross stream type catheter tube which uses direct fluid jet streams as the outflow component.

Another significant aspect and feature of devices of the present disclosure is the use of direct fluid jet stream devices that operate with or without evacuation capabilities.

Another significant aspect and feature of devices of the present disclosure is the use of a catheter tube and a manifold that may be used with any sized guidewire.

Another significant aspect and feature of devices of the present disclosure is the use of direct fluid jet stream velocities ranging from 1 to 250 m/s.

Another significant aspect and feature of devices of the present disclosure is the use of direct fluid jet streams emanating from orifices of 0.001 inch to 0.040 inch in diameter.

Having thus briefly described one or more embodiments of this disclosure, and having mentioned some significant aspects and features, it is the principal object of this disclosure to provide a direct stream hydrodynamic catheter system.

BRIEF DESCRIPTION OF THE DRAWINGS

Other objects of the disclosure and many of its attendant advantages will be readily appreciated as the same becomes better understood by reference to the following detailed description when considered in connection with the accompanying drawings, in which like reference numerals designate like parts throughout the figures thereof and wherein.

DETAILED DESCRIPTION

Figure 1:
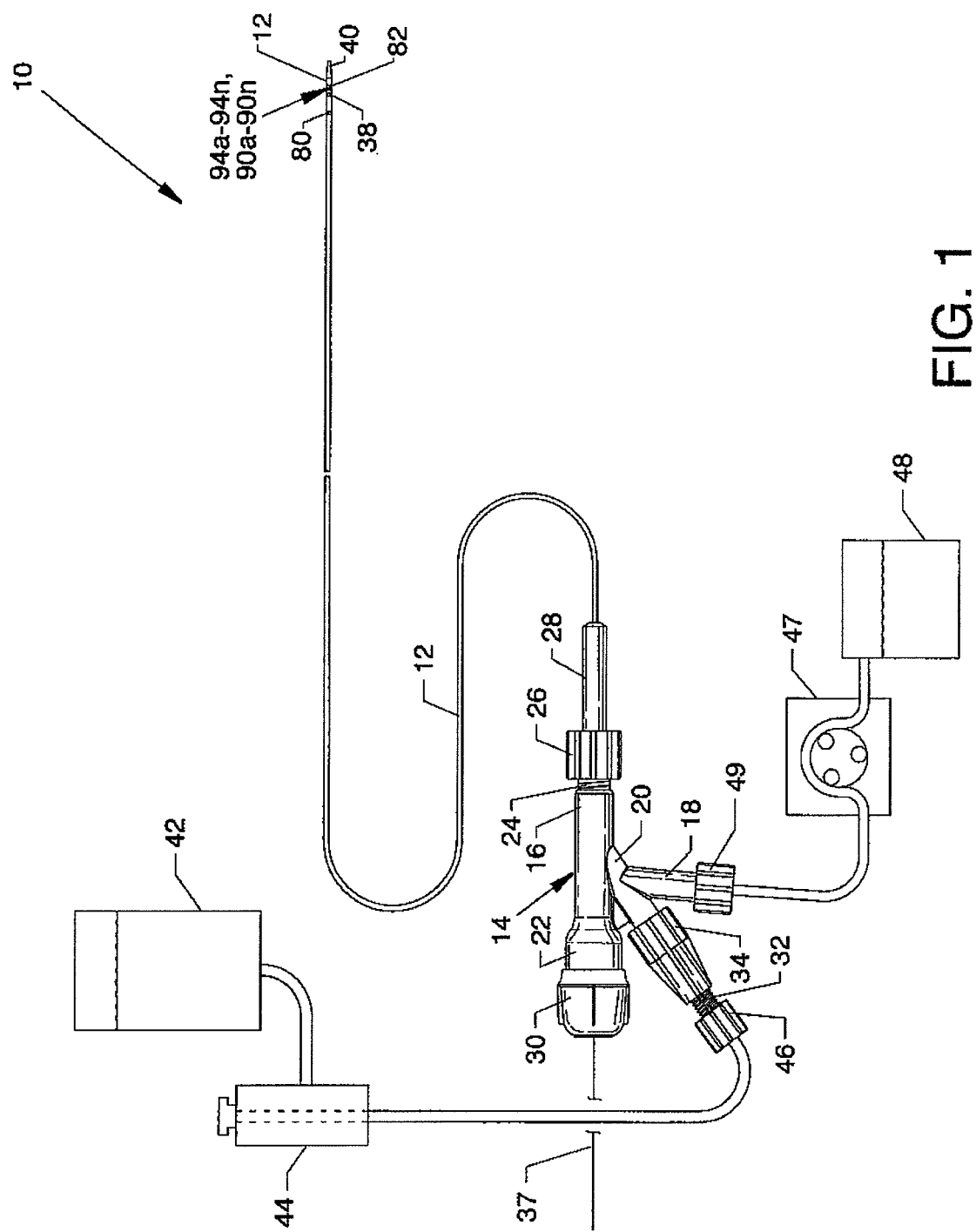
FIG. 1 is a plan view of the visible components of a direct stream hydrodynamic catheter system.
Figure 2:
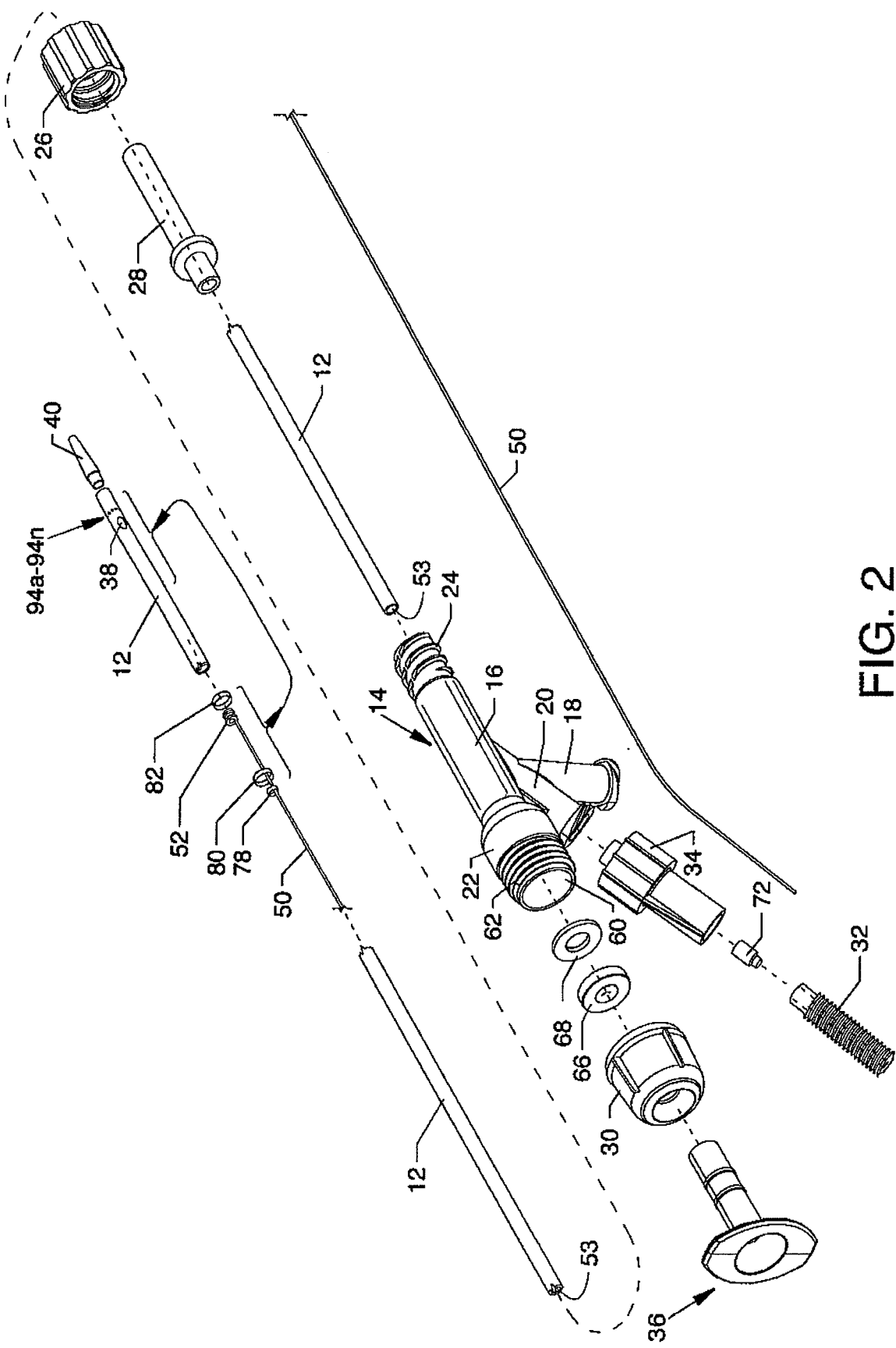
FIG. 2 generally is an isometric exploded and segmented view of a catheter tube and a manifold which are used with enabling components shown in FIG. 1.

FIG. 1 is a plan view of the visible components of a direct stream hydrodynamic catheter system 10, which can also be referred to for purposes of brevity as the catheter system 10. The system includes a direct stream hydrodynamic catheter tube 12, also referred to as the catheter tube 12, in association with a one-piece manifold 14, the latter having multiple structures extending therefrom or attached thereto including, but not limited to, the flexible multiple feature catheter tube 12. The visible portion of the one-piece manifold 14 includes a central tubular body 16, a threaded exhaust branch 18, and a high pressure connection branch 20 extending angularly from the central tubular body 16, a partially shown cavity body 22 extending proximally from the central tubular body 16 and a threaded connection port 24 extending distally from the central tubular body 16. The proximal end of the catheter tube 12 is secured to the manifold 14 by the use of a Luer fitting 26 accommodated by the threaded connection port 24. The proximal end of the catheter tube 12 extends through a strain relief tube 28 and through the Luer fitting 26 to communicate with the manifold 14. Also shown is a hemostasis nut 30 in alignment with and threadingly engaged with the proximal region of the cavity body 22. A threaded high pressure connection port 32 is secured to the high pressure connection branch 20 by a Luer connector 34. An introducer 36 is shown in FIG. 2. A guidewire 37, in association with the disclosure, is shown in FIG. 3.

The catheter tube 12 extends distally from the manifold 14 and includes an inflow orifice 38 at the distal section of the catheter tube 12. In the alternative, an inflow gap could be provided in lieu of the inflow orifice 38. A tapered flexible tip 40 extends distally from the distal section of the catheter tube 12 and is secured thereto and therein. The catheter tube 12 functions as an exhaust tube for the evacuation of thrombus or lesion particulate, fluids or other debris or effluent from the thrombus or lesion site. Preferably, the catheter tube 12 includes a hydrophilic coating to enhance deliverability along the vasculature or other structure.

Enabling components provide for the operation and utilization of the catheter tube 12, the manifold 14 and components closely related thereto and therein include a high pressure fluid source 42 and a high pressure fluid pump 44 connected to the manifold 14 via the threaded high pressure connection port 32 and connector 46. Also included are an exhaust regulator 47 in the form of a roller pump or other suitable device and a collection chamber 48 connected to the threaded exhaust branch 18 by a connector 49 as shown.

Figure 3:
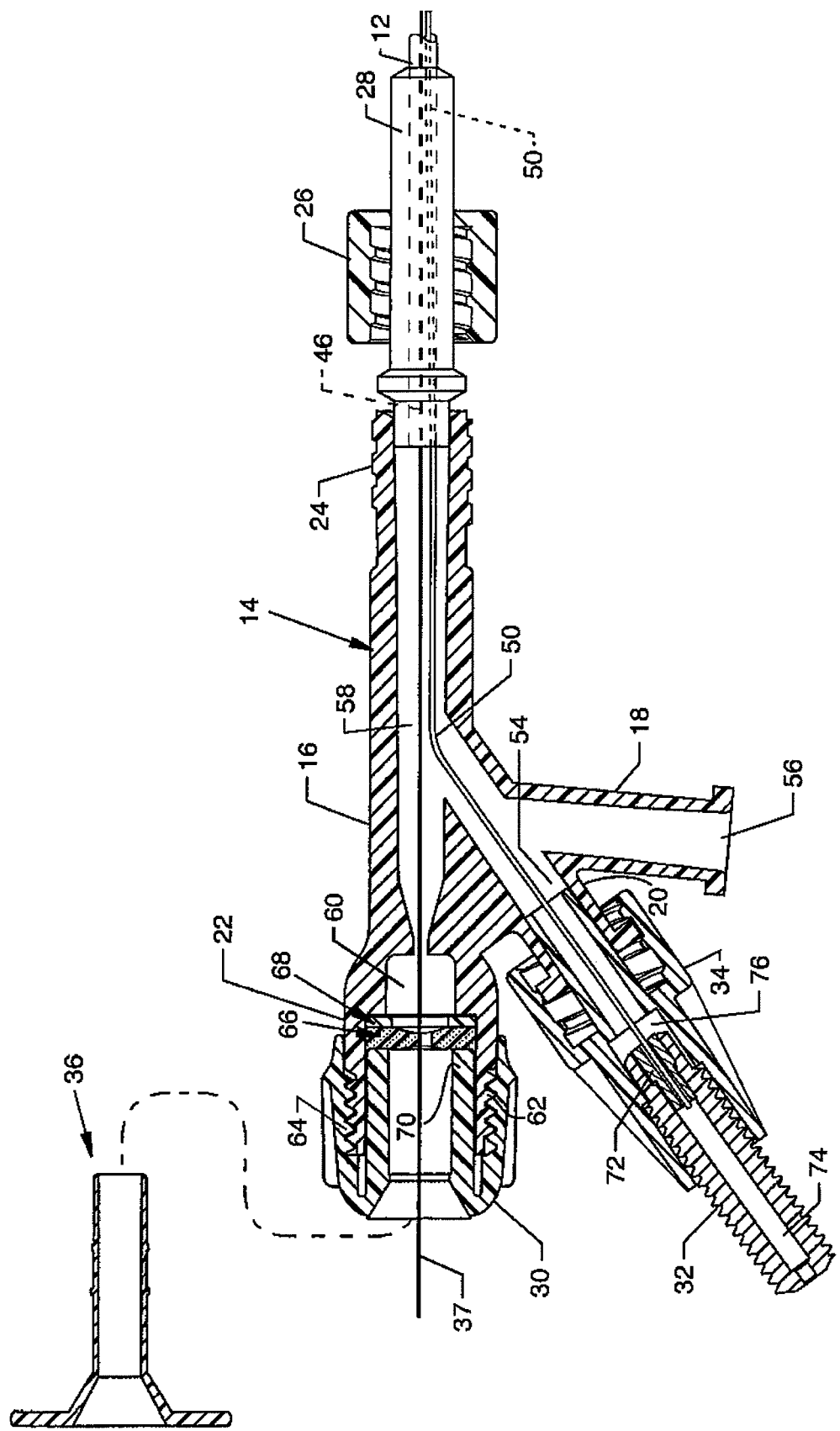
FIG. 3 is an assembled view, in partial cross section, of the components of the manifold and closely associated components and features thereof.

FIGS. 2 and 3 show portions of the disclosure. FIG. 2 generally is an isometric exploded and segmented view of the catheter tube 12 and the manifold 14 which are used with the enabling components shown in FIG. 1. FIG. 3 is an assembled view, in partial cross section, of the components of the manifold 14 and closely associated components and features thereof. Also included is a guidewire 37 incorporated into the use thereof.

A group of assembled components, including a high pressure tube 50 and a fluid jet emanator 52, deliver pressurized saline or other suitable fluid to the distal section of the catheter tube 12 for producing fluid jet streams which are directed radially from the fluid jet emanator 52, as later described in detail. The high pressure tube 50, preferably of flexible stainless steel or other suitable material, extends within closely associated features or components attached to the manifold 14 and passes therethrough and is aligned with and distal to the strain relief tube 28. The high pressure tube 50 extends along a greater portion of and within a lumen 53 of the catheter tube 12 to terminate at the fluid jet emanator 52. The distal end of the high pressure tube 50, including the fluid jet emanator 52, is also shown in greater detail in FIGS. 4 and 5.

As provided in FIGS. 2 and 3, the manifold 14, which is also used with reference to the alternative embodiments, has connected and communicating passageways and cavities (FIG. 3) including a high pressure connection branch passageway 54, an exhaust branch passageway 56, a tapered central passageway 58 extending from and through the threaded connection port 24 and through the central tubular body 16 to and communicating with a multiple radius cavity 60, which preferably is cylindrical and located central to the cavity body 22. External threads 62 are located about the proximal portion of the cavity body 22 at the proximal region of the manifold 14 for accommodating the internal threads 64 of the hemostasis nut 30.

Beneficial to devices of the disclosure is the use of a flexible self-sealing hemostasis valve 66 and the use of a washer 68 which is located distal to the self-sealing hemostasis valve 66, the shape and function of which are described in referenced U.S. Pat. No. 7,226,433 which is incorporated herein in its entirety. The self-sealing hemostasis valve 66 and the washer 68 are aligned within the greater radius portion of the multiple radius cavity 60 of the cavity body 22. The hemostasis nut 30 includes a centrally located cylindrical boss 70. The washer 68 and the self-sealing hemostasis valve 66 are captured within the greater radius portion of the multiple radius cavity 60 by the threaded engagement of the hemostasis nut 30 to the threads 62 at the proximal end of the manifold 14. The cylindrical boss 70 is brought to bear against the collective self-sealing hemostasis valve 66 and the washer 68 bringing pressure to bear, as required, against the self-sealing hemostasis valve 66 which pressure culminates in a forcible sealing of the self-sealing hemostasis valve 66 about the guidewire 37. Although one method of sealing against a guidewire is briefly shown and described herein, it is appreciated that other methods can be incorporated into this and other forms of the present disclosure such as those methods referenced in U.S. Pat. No. 7,226,433.

Also shown is a ferrule 72 which is aligned within a passageway 74 of the threaded high pressure connection port 32, the combination of which is partially aligned within an interior passageway 76 of the Luer connector 34. The proximal end of the flexible high pressure tube 50, shown in segmented form in FIG. 2, is used for the delivery of nominal or high pressure ablation liquids or for the delivery of drugs or other liquids and is suitably secured in a central passageway of the ferrule 72 to communicate with the interior passageway 74 of the threaded high pressure connection port 32, as shown in FIG. 3. The proximal end of the high pressure tube 50 also extends through the high pressure connection branch passageway 54, through part of the tapered central passageway 58, through the strain relief tube 28 and Luer fitting 26, and through the lumen 53 of the catheter tube 12.

Figure 4:
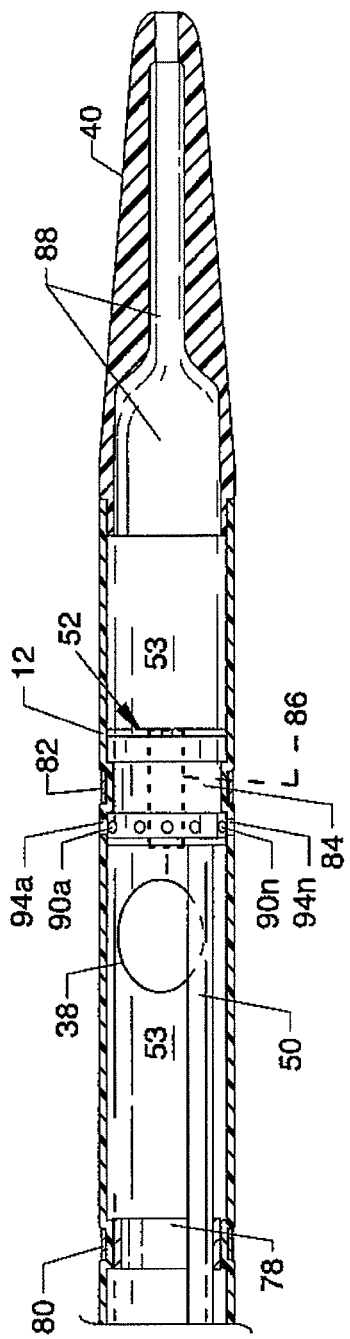
FIG. 4 illustrates the distal portion of the catheter tube and the relationships of radiopaque marker bands, a support ring, a high pressure tube, and a fluid jet emanator to each other and to the catheter tube.

As shown in FIG. 4, the high pressure tube 50 extends through a support ring 78 and is suitably attached thereto to provide an anchoring and alignment structure for the high pressure tube 50 thereby affixing the distal portion of the high pressure tube 50 within the distal end of the catheter tube 12. In addition, the high pressure tube 50 also extends indirectly through the radiopaque marker band 80. The concentrically aligned radiopaque marker band 80 and the support ring 78 are shown forcibly contacting the full wall thickness of the catheter tube 12 at the distal end of the catheter tube 12. The high pressure tube 50 is preferably attached to the support ring 78, such as by welding or other suitable means, where the support ring 78 functions as a support for the catheter tube 12 in the region beneath the radiopaque marker band 80. The high pressure tube 50 extends across the inflow orifice 38 and terminates within an internal annular manifold (not shown) of the fluid jet emanator 52 and is suitably attached thereto where the interior cavity (not shown) of the fluid jet emanatory 52 communicates with the lumen of the high pressure tube 50, such as in the closely related fluid jet emanator described in the previously referenced U.S. Pat. No. 7,879,022 or other applications or patents assigned to the assignee. The fluid jet emanator 52, also shown in FIG. 5 as an isometric view, includes an annular groove 84 which is in coordinated use with a radiopaque marker band 82 to secure the fluid jet emanator 52 within the distal section of the catheter tube 12. The distally located radiopaque marker band 82 is forcibly applied around the distal end of the catheter tube 12 to cause a frictional annular engagement with all or part of the annular grove 84 of the fluid jet emanator 52. Such frictional engagement is sufficient to place the outer radial surface of the radiopaque marker band 82 (also 80) in a position lesser than the general and greater outer radial surface of the catheter tube 12, thereby providing, in part, a catheter tube 12 having no elements protruding beyond the general outer radial surface thereof for an unimpeded and smooth distal or proximal transition of the catheter tube 12 within a vein, artery or the like. A passageway 86 (FIG. 5) is shown central to the fluid jet emanator 52 to accommodate the passage of a guidewire 37 (shown in FIG. 3). The tapered flexible tip 40 is shown suitably secured to the distal end of the distal section for the catheter tube 12. The tapered flexible tip 40 includes a multiple radius inner passageway 88 for the accommodation of a guidewire 37. In FIG. 2, the radiopaque marker band 80 is shown displaced a short distance distal to the support ring 78 and the fluid jet emanator 52 is shown displaced proximally a short distance from the radiopaque marker band 82 for the purpose of clarity, but are shown in frictional engagement in their actual positions along and with respect to the distal end of the catheter tube 12 in FIG. 4. The relationships of the radiopaque marker bands 80 and 82, the support ring 78, and the fluid jet emanator 52, respectively, to each other and of the catheter tube 12, are shown best in FIG. 4.

Structure is provided to nurture and aid the introduction and passage of the distal portion of the catheter tube 12 through blood vessels, arteries and the like to the sites of deposits of thrombus or lesions. The tapered flexible tip 40, as opposed to a rounded and nontapered flexible tip, can part and more easily penetrate deposits of thrombus or lesions during its insertional travel in a distal direction instead of advancing or pushing such deposits of thrombus or lesions distally. The decreasing diameter in a distal direction of the tapered flexible tip 40 also allows for an increased flexibility in negotiating and passing through tortuous paths.

The exhaust tube support ring 78 in use with the radiopaque marker band 80 and the use of the fluid jet emanator 52 with the marker band 82 within and about the proximal and distal sections of the catheter tube 12, respectively, are examples of structures offering support or reinforcement along the catheter tube 12. Such a support ring 78, marker bands 80 and 82, and the external structure of the fluid jet emanator 52 provide for the use of a thinner wall thickness for the catheter tube 12 and allow for a larger and more effective and efficiently sized lumen 53 of the catheter tube 12, as well as contributing to a reduced sized outer diameter. Such support rings and external structure of the fluid jet emanator 52 also contribute to supportively maintain the diameter and overall shape of the catheter tube 12 when the catheter tube 12 is pushed or advanced along a vein or artery, as well as aiding in torsional support.

Figure 5:
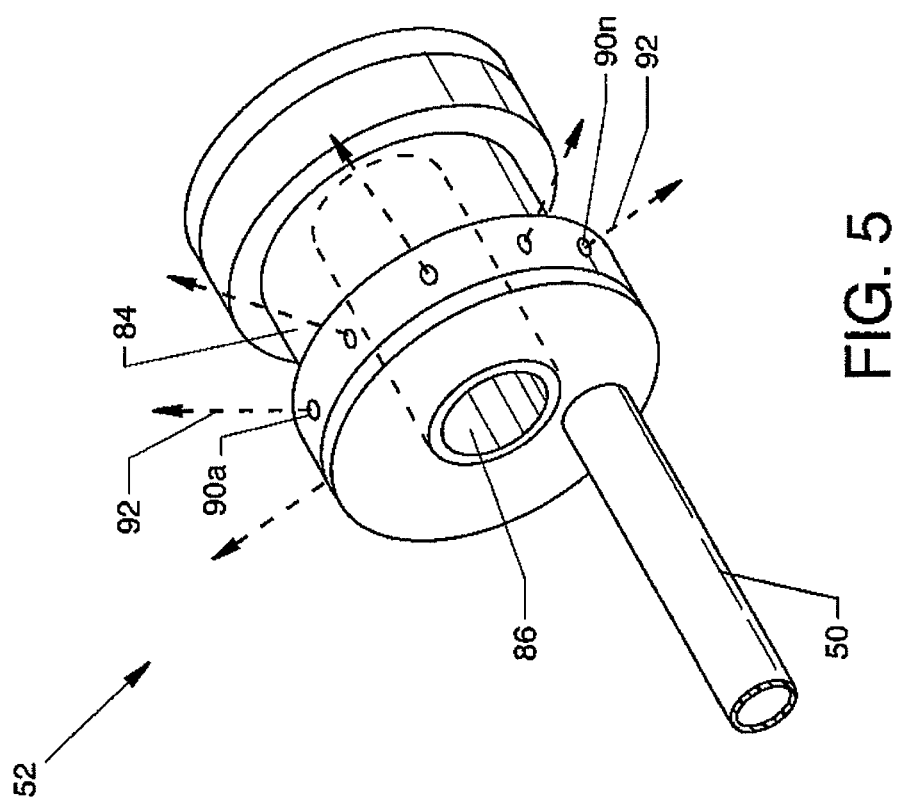
FIG. 5 is an isometric view of the fluid jet emanator shown connected to and in communication with a high pressure tube.

FIG. 5 is an isometric view of the fluid jet emanator 52 shown connected to and in communication with the high pressure tube 50. The fluid jet emanator 52 includes a plurality of like and nominal sized radially directed jet orifices 90$a$-90$n$ located around the periphery of the fluid jet emanator as well as including the previously described annular groove 84 and passageway 86. The plurality of radially directed jet orifices 90$a$-90$n$ are in common and are pressurized in common by pressured saline provided through the high pressure tube 50.

The high pressure tube 50 delivers high pressure saline or other suitable fluid to the fluid jet emanator 52 for producing and distributing high pressure and nominally sized radially directed fluid jet streams 92 of saline or other suitable fluids which emanate from the radially directed jet orifices 90$a$-90$n$ of the fluid jet emanator 52 to perform functions, as described herein. A plurality of holes 94$a$-94$n$ corresponding to and in alignment with the radially directed jet orifices 90$a$-90$n$ are provided in the distal end of the catheter tube 12, as shown in FIG. 4, or in alternative embodiments in order to allow the passage of the radially directed fluid jet streams 92 therethrough. Although the use of the particular style of fluid jet emanator 52 is shown, other fluid jet emanators having other configurations emanating radially directed fluid jet streams 92 can also be used in lieu of the fluid jet emanator 52 shown in FIG. 5 and the use of other fluid jet emanators shall not be considered to be limiting to the scope of the disclosure.

Mode of Operation

Generally, a normal guidewire is deployed in a blood vessel 96 requiring treatment or, in the alternative, a filter guidewire or balloon occlusion guidewire could also be used. The catheter tube 12 and other closely associated and aligned components directly associated therewith consisting mainly of the high pressure tube 50 and the fluid jet emanator 52 are advanced over and along a guidewire (37) which is aligned within the blood vessel 96 for the purpose of debris/thrombus/lesion removal, drug infusion, or other procedures and maneuvered into an appropriate position for treatment. A generic guide catheter or sheath can be incorporated as necessary to offer assistance in placing the catheter tube 12 and closely aligned components in direct association therewith of the direct stream hydrodynamic catheter system 10 within the desired location of the blood vessel 96 in order that the tapered tip 40 of the catheter tube 12 can be extended through the thrombus or lesions 98 to position the fluid jet emanator in very close proximity to the thrombus or lesions 98. The catheter tube 12 may be moved proximally or distally during the procedure to maximize the effect of the catheter system. Further interventions can be executed as normal over the remaining guidewire or guidewire device.

Figure 6:
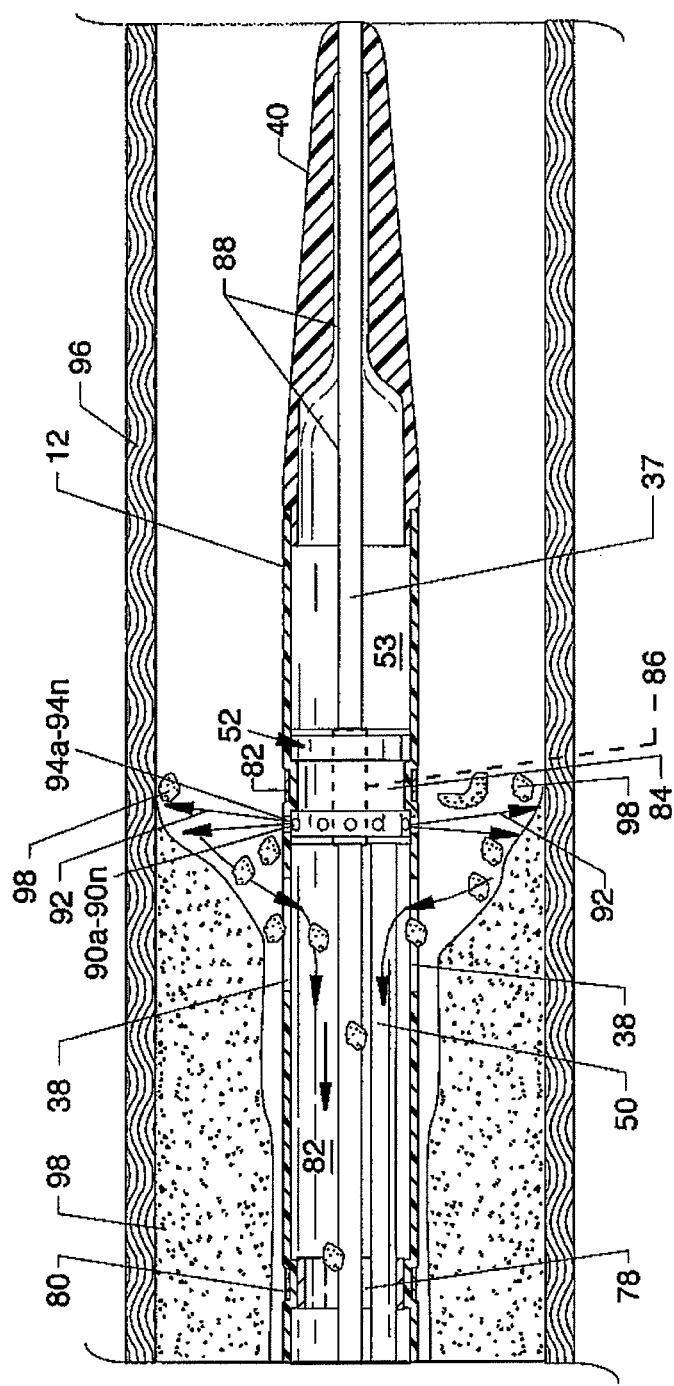
FIG. 6 is a side view, in partial cross section, of the distal portion of the catheter tube in the performance of the method and use thereof which performance utilizes enabling connections and which utilizes functions of the accompanying components in a manner as shown in FIG. 1.

Moreover, FIG. 6 is a side view, in partial cross section, of the catheter tube 12 in the performance of the method and use thereof which utilizes enabling connections and which utilizes functions of the accompanying components in a manner as shown in FIG. 1 with particular attention given to the distal section of the catheter tube 12, the flexible tapered tip 40, the fluid jet emanator 52, the inflow orifice 38, and other closely associated components positioned in the blood vessel 96 containing deposits of thrombus or lesions 98. More specifically and with reference to FIGS. 1 and 6, the mode of operation is further described in use. The direct stream hydrodynamic catheter tube 12 is engaged over and about a guidewire 37 wherein the guidewire 37 (previously inserted into a vein or artery) can first slideably pass through the passageway 88 of the tapered flexible tip 40, into and through the lumen 53 of the catheter tube 12, followed by transiting the passageway 86 of the fluid jet emanator 52, past the inflow orifice 38, followed by transiting the lumen 53 of the catheter tube 12, the strain relief tube 28, the tapered central passageway 58 of the manifold 14 (FIG. 3) and slideably within and in sealed engagement with the hemostasis valve 66 (FIG. 3) to finally exit from the hemostasis nut 30.

The distal portion of the high pressure tube 50 delivers pressurized saline or other suitable fluid to the fluid jet emanator 52 to produce and distribute, preferably, non-hemolyzing radially directed fluid jet streams 92 of saline or other suitable fluids which emanate as direct fluid jet streams from the radially directed jet orifices 90a-90n of the fluid jet emanator 52 in order to accomplish thrombectomy functions, as described herein. Carefully generated operating pressure and fluid flows at values short of hemolysis can be provided primarily by controlling the input fluid pressure at the high pressure fluid pump 44 and/or by controlling the exhaust rate at the exhaust regulator 47, whereby the exhaust regulator 47 is operated to provide a negative pressure for effluent aspiration. Other fluid jet emanators of appropriate size and/or configuration can also be incorporated in lieu of the fluid jet emanator 52 within the distal section of the catheter tube 12 to emanate or emit one or more radially directed fluid jet streams 92.

The use of the radially directed fluid jet streams 92 from the radially directed jet orifices 90a-90n provides for the fluid jet impingement of the deposits of thrombus or lesions of 98 on the inner wall of the blood vessel 96 adjacent to or in close proximity to the radially directed jet orifices 90a-90n in order to impinge, ablate and loosen deposits of thrombus or lesions 98, whereby such thrombus or lesion particulate and fluids can be entrained through one or more inflow orifices 38 by aspiration involving the use of an exhaust regulator 47 to be exhausted proximally through the catheter tube 12. Alternatively, manual aspiration methods as well known in the art can be utilized as well. Additionally, drugs for treatment or for lysing of the thrombus or lesions 98 can also be delivered via the radially directed jet orifices 90a-90n and radially directed fluid jet streams 92 in order to soften the deposits of thrombus or lesions 98 in the region of the blood vessel 96 adjacent to or in close proximity to the radial jet orifices 90a-90n, thereby benefiting and making use of the radially directed fluid jet streams 92 more effective. The drugs are delivered through the high pressure tube 50 to the sites of the deposits of thrombus or lesions 98 using the fluid jet emanator 52.

One or more inflow orifices 38 receive, ingest and entrain thrombus or lesions 98 in the form of particulate and/or debris therethrough by fluidic flow and are entrained to be urged and carried along the lumen 53 of the catheter tube 12 by aspiration involving the exhaust regulator 47, wherein the entrainment of thrombus or lesions 98 particulate and/or debris through the inflow orifice(s) 38 is influenced by and based on entrainment in association with aspiration in coordination with the exhaust regulator 47 through the catheter 12. In such a device, the inflow orifice 38 is sufficiently sized for aspiration or multiple inflow orifices may be used in order to achieve a desired fluid inflow and aspiration. The outflow of fluid and thrombus or lesions is driven proximally through the catheter tube 12 by an internal pressure which results from the radially directed fluid jet streams 92 and the fluid entrained through the inflow orifice 38 and is assisted by aspiration by use of the exhaust regulator 47.

As herein disclosed, the radially directed fluid jet streams 92 are driven by the same pressure source where the velocity is controllingly influenced by the high pressure pump 44 and the total area of all of the radially directed jet orifices 90a-90n. By sizing the radially directed jet orifices 90a-90n and operating the high pressure pump 44 within suitable parameters, the velocity and strength of the radially directed jet streams 92 can be influenced and controlled. The use of nominally sized radially directed jet orifices 90a-90n provides for fluid jet streams having enough momentum which can be delivered by a large non-hemolysing fluid jet streams (92) which are equivalent in energy, via an increased flow rate, to a high velocity, smaller, fluid jet stream to be described later. The principle for an aggressive debris removal is dependent on the velocity of the radially directed jet streams 92. Consider that there is some critical velocity for debris liberation. As the radially directed jet streams 92 travel through a fluid environment, the jet streams will entrain surrounding fluid whereby the velocity of the fluid jet streams will slow. There are empirical relationships for turbulent jet streams that show that velocity is proportional to the diameter of the jet streams and to the initial velocity of the jet streams. Thus, the velocity at a given distance would be increased by either increasing the initial jet stream velocity or increasing the jet orifice diameter. Note that if the jet orifice diameter is increased, the pump rate of the high pressure pump 44 would need to be increased in order to maintain the fluid jet stream velocity. In practice, the catheter system is designed with a given set of jet orifice diameters and the high pressure pump 44 pump rate is adjusted to achieve the proper efficacy.

In general, the structure and operation of embodiments disclosed herein provide for radially directed jet orifices in a size range from 0.001 inch to 0.040 inch for emanation of saline or other suitable fluid therefrom at a velocity range of 1 to 250 m/s. Proximally directed jet orifices can range in size from 0.001 inch to 0.040 inch for emanation of saline or other suitable fluid therefrom in a velocity range of 1 to 250 m/s. Distally directed jet orifices where used can range in size from 0.001 inch to 0.040 inch for emanation of saline or other suitable fluid therefrom in a velocity range of 1 to 250 m/s. By sizing the radially directed jet orifices and adjusting the high pressure fluid pump, the velocity and strength of the radially directed jet stream can be controlled. Also, the radially directed jet orifices can be sized such that the velocity of the jet streams is decreased to a point where no red blood cells are hemolysed, but the momentum of the jet streams can then be increased by means of an infused volume such that the efficacy of the catheter system is as high as that of the high velocity thrombectomy catheters disclosed in Applicant's related references as set forth above. The general operating pressure of the catheter system can range from 50 psi to 20,000 psi. Generally, those catheter systems of the embodiments disclosed herein use nominal sized radially directed jet orifices 90a-90n to emanate radially directed fluid jet streams 92, and the fourth alternative embodiment utilizes cross stream jets 132 (FIG. 22) where the occurrence of hemolysis is not desired or is to be minimized. Other embodiments can use smaller sized radially directed jet orifices 112a-112n (shown later) to emanate radially directed fluid jet streams 92 of greater strength and efficacy.

Figure 7:
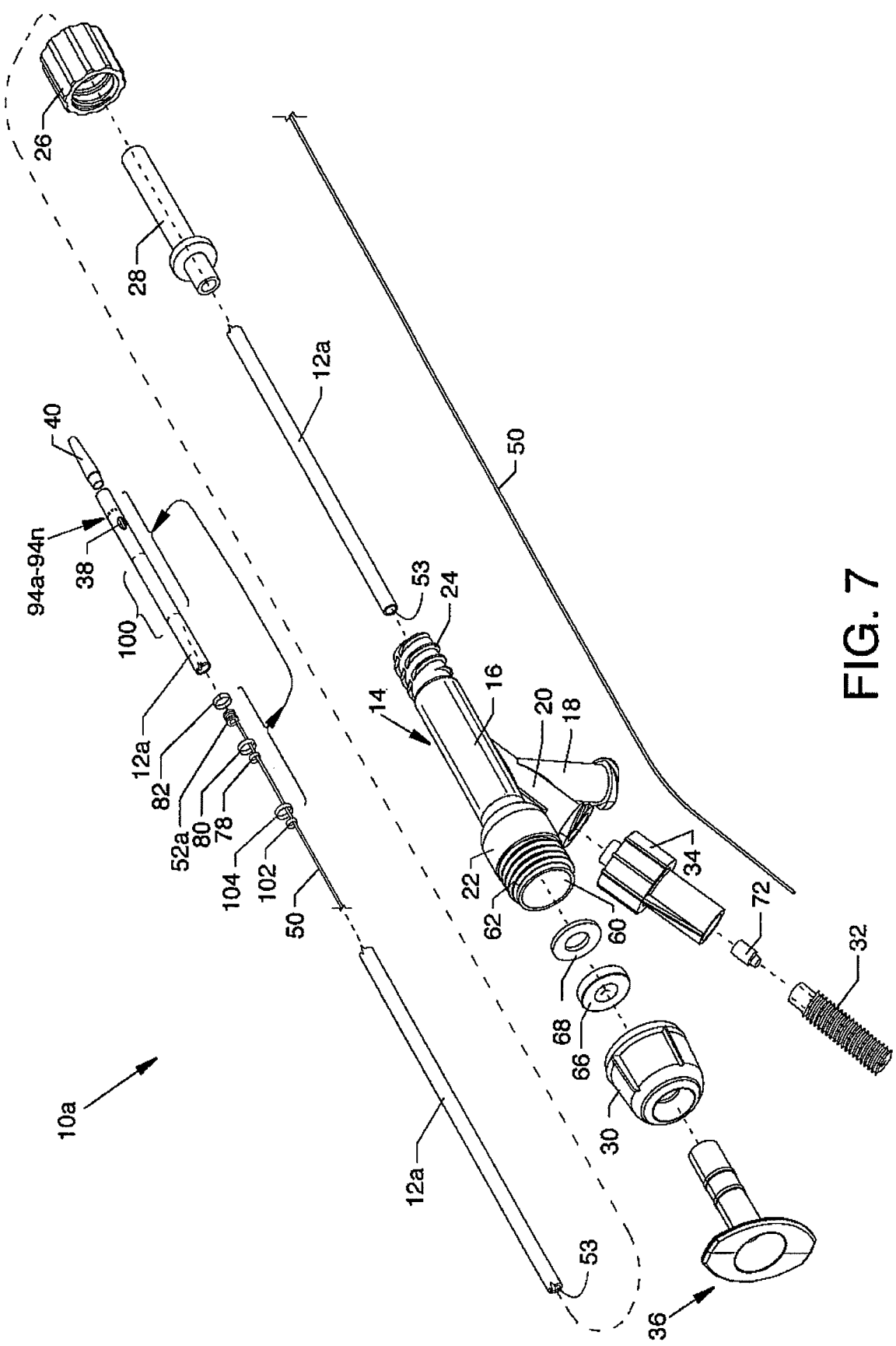
FIG. 7, a first alternative embodiment, generally is an isometric exploded and segmented view of a catheter tube and a manifold which are used with enabling components shown in FIG. 1.

FIG. 7, a first alternative embodiment, is an illustration similar in many respects to FIG. 2 showing a direct stream hydrodynamic catheter tube 12a, also referred to as the catheter tube 12a, and the manifold 14 and components associated therewith and wherein each is connected to and utilizes functions of the accompanying enabling components in a manner similar to that shown in FIG. 1 where all numerals correspond to those elements previously described or as otherwise described herein. The catheter tube 12 is reconfigured as a catheter tube 12a to additionally include a balloon 100, which is self-inflating, located at the distal end thereof and at a position proximal to the inflow orifice 38. A support ring 102 is additionally included and is secured to the high pressure tube 50. A marker band 104 is also additionally included and is coaxially and indirectly aligned with the support ring 102, as later described in detail. The components of FIG. 7 are used with the enabling components referred to and shown in FIG. 1 where such enabling components consist of the high pressure fluid source 42, the high pressure fluid pump 44, the threaded high pressure connection port 32 and connector 46, the exhaust regulator 47, the collection chamber 48 and the connector 49 which are used much in the same manner as previously described. Together, the referenced enabling components in combination with the catheter tube 12a and the manifold 14 and closely associated components thereof comprise a direct stream hydrodynamic catheter system 10a which is also referred to as the catheter system 10a. Although the catheter tube 12a, the manifold 14, and closely associated components of each are shown referenced to the catheter system 10a in FIG. 7, it is understood that the previously referenced enabling components referred to and shown in FIG. 1, but not shown in FIG. 7, are also part of the catheter system 10a.

Figure 8:
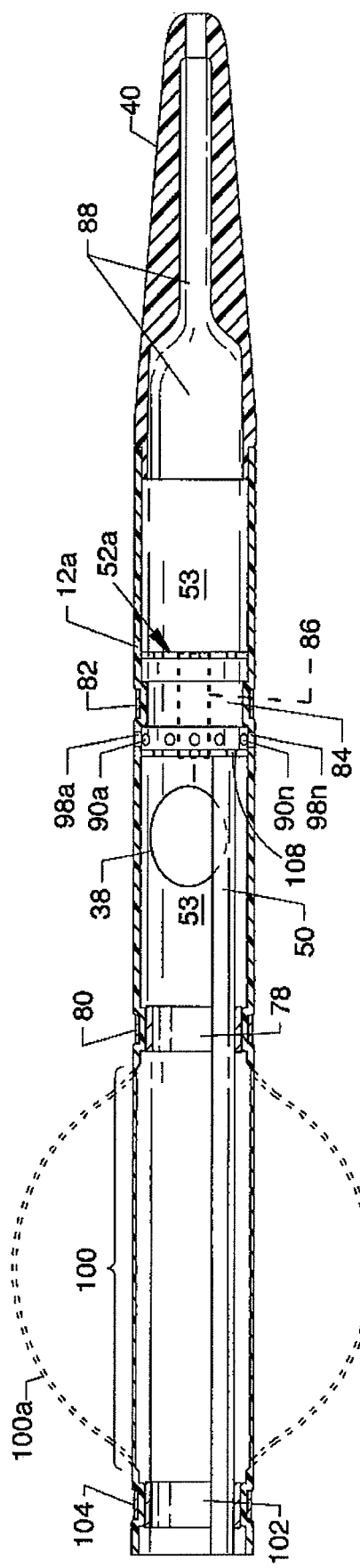
FIG. 8 is an illustration similar in many respects to FIG. 4 showing the distal portion of the catheter tube and the relationships of radiopaque marker bands, a support ring, a high pressure tube, a fluid jet emanator, and a balloon to each other and to the catheter tube.

As shown in FIG. 8, the high pressure tube 50 also extends through the support ring 102 and is suitably connected thereto to provide for an additional anchoring and alignment structure for the high pressure tube 50 in order to affix the distal portion of the high pressure tube 50 within the distal end of the catheter tube 12a. In addition, the high pressure tube 50 also extends indirectly through the radiopaque marker band 104. The concentrically aligned radiopaque marker band 104 and the support ring 102 are shown forcibly contacting the full wall thickness of the catheter tube 12a proximal to the balloon 100. As previously described, the high pressure tube 50 preferably is attached to the support ring 78, such as by welding or other suitable means, where the support ring 78 functions as a support for the catheter tube 12a in the region beneath the radiopaque marker band 80. The high pressure tube 50 extends across the inflow orifice 38 and terminates within an internal annular manifold (not shown) of the fluid jet emanator 52a and is suitably attached thereto where the fluid jet emanator 52a communicates with the lumen of the high pressure tube 50. The balloon 100 which is continuous with the catheter tube 12a, preferably has a wall thickness less than that of the general wall thickness of the catheter tube 12a, is aligned in a longitudinal orientation between the coaxially aligned marker band 104 and support ring 102 and the aligned marker band 80 and support ring 78. The profile of the balloon 100 in the inflated mode is shown in dashed lines and referenced as the inflated balloon 100a.

Figure 9:
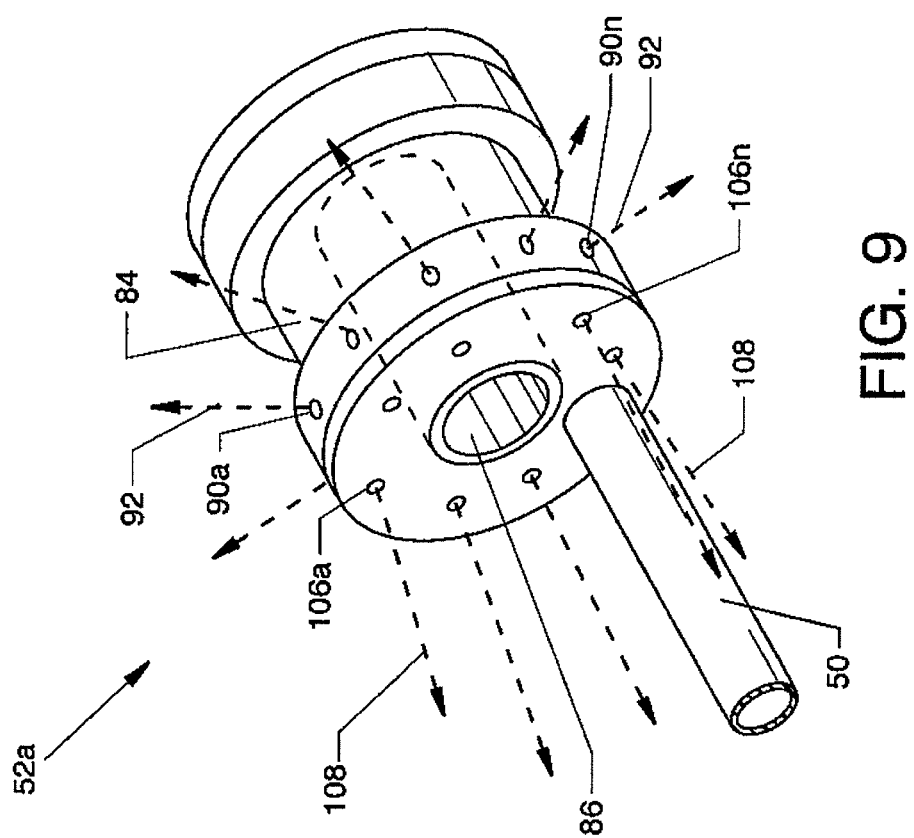
FIG. 9 is an illustration similar in many respects to FIG. 5 and is an isometric view of another fluid jet emanator shown connected to and in communication with a high pressure tube.

FIG. 9 is an illustration similar in many respects to FIG. 5 showing an isometric view of an alternative fluid jet emanator 52a connected to and in communication with the high pressure tube 50. In addition to the previously shown and described plurality of like and nominal sized radially directed jet orifices 90a-90n, the fluid jet emanator 52a also includes a plurality of proximally (rearwardly) directed orifices 106a-106n located on and about a proximal face of the emanator 52a and in parallel alignment to the longitudinal axis of the fluid jet emanator 52a, as well as including the previously described annular groove 84 and passageway 86. The plurality of radially directed jet orifices 90a-90n and the plurality of proximally directed jet orifices 106a-106n are in common and are pressurized in common by pressured saline provided through the high pressure tube 50. The high pressure tube 50 delivers a pressurized saline or other suitable fluid to the fluid jet emanator 52a for producing and distributing nominal sized radially directed fluid jet streams 92 of saline or other suitable fluids which emanate from the radially directed jet orifices 90a-90n of the fluid jet emanator 52a to perform functions, as described herein. The fluid jet emanator 52a also provides and distributes pressurized proximally directed fluid jet streams 108 of saline or other suitable fluids which are directed proximally from the proximally directed orifices 106a-106n to perform functions, as described herein.

Mode of Operation

Figure 10:
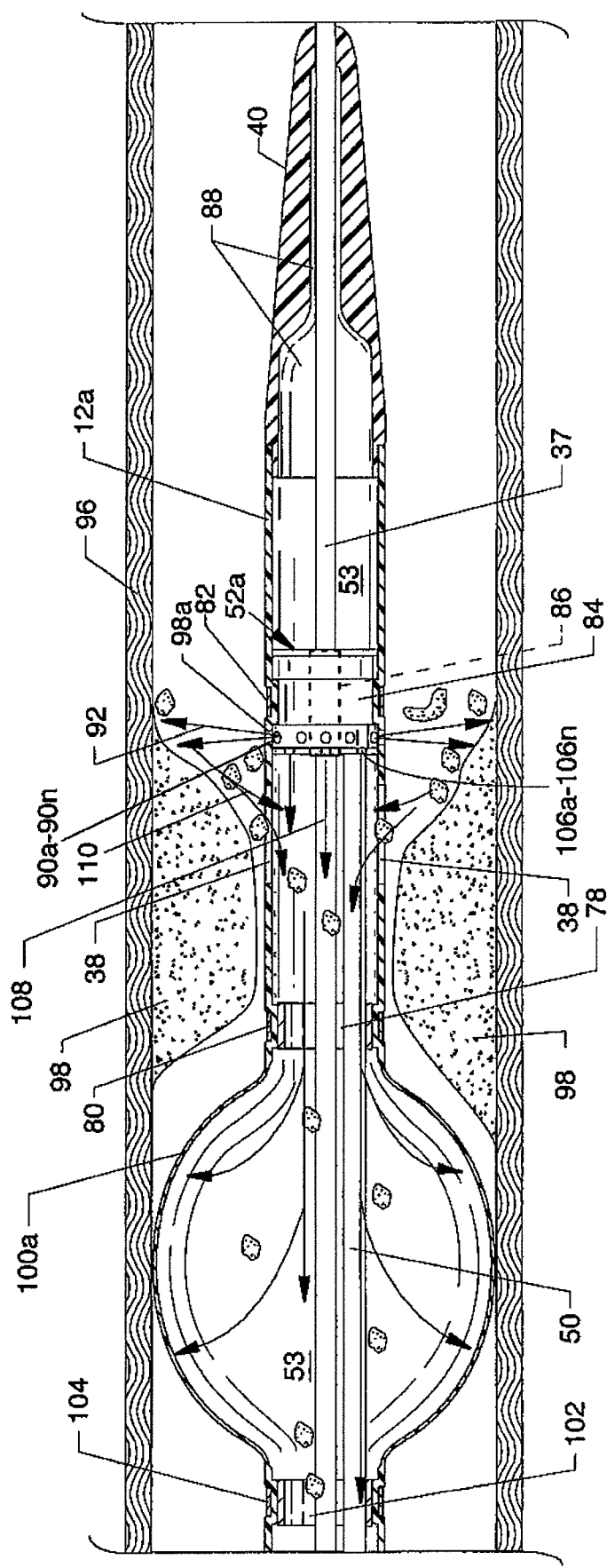
FIG. 10 is similar in many respects to FIG. 6 and is a side view, in partial cross section, of the distal portion of the catheter tube in the performance of the method and use thereof which performance utilizes enabling connections and which utilizes functions of the accompanying components in a manner as shown in FIG. 1.

In a closely related fashion and manner as previously described and with reference to FIG. 10, the method of operation of a first alternative embodiment is now described. Generally, a normal guidewire 37 is deployed in a blood vessel 96 requiring treatment, or in the alternative, a filter guidewire or balloon occlusion guidewire could also be used. The catheter tube 12a and other closely associated and aligned components directly associated therewith consisting mainly of the high pressure tube 50, the fluid jet emanator 52a, the distal section of the catheter tube 12a, and the uninflated balloon 100 are advanced over and along the guidewire 37 and aligned within the blood vessel 96 for the purpose of debris/thrombus/lesion maceration and removal, drug infusion, or other procedures and maneuvered into an appropriate position within the blood vessel 96 for treatment. A generic guide catheter or sheath can be incorporated as necessary to offer assistance in placing the catheter tube 12a and closely aligned components in direct association therewith of the direct stream hydrodynamic catheter system 10a within the desired location of the blood vessel 96 in order that the tapered flexible tip 40 of the catheter tube 12a can be extended through and beyond the thrombus or lesions 98 to position the fluid jet emanator 52a in very close proximity to the thrombus or lesions 98 and to place the self-inflating balloon 100 proximal to the thrombus or lesions 98. The direct stream thrombectomy catheter system 10a is then activated, wherein the balloon 100 is automatically and expandingly deployed reforming as an expanded balloon 100a, and then thrombus, debris and the like are removed or drugs can be infused by a desired procedure.

Moreover, FIG. 10 is a side view, in partial cross section, of the catheter tube 12a of the first alternative embodiment illustrating the performance of the method and use thereof which performance utilizes enabling connections and which performance utilizes functions of the accompanying components in a manner similar to that shown in FIG. 1 with particular attention given to the distal section of the catheter tube 12a, the flexible tapered tip 40, the inflated self-inflated balloon 100a, the fluid jet emanator 52a, the inflow orifice(s) 38 (reoriented), and other closely associated components positioned in the blood vessel 96 containing deposits of thrombus or lesions 98. For purposes of example and illustration, one or more inflow orifice(s) 38 are shown at the top and the bottom of the catheter tube 12a. More specifically and with reference to FIG. 10, the mode of operation is further described. In use, the direct stream hydrodynamic catheter tube 12a can be engaged over and about the guidewire 37, wherein the guidewire 37 (previously inserted into a vein or artery) can first slideably pass through the passageway 88 of the tapered flexible tip 40, into and through the lumen 53 of the catheter tube 12a, followed by transiting the passageway 86 of the fluid jet emanator 52a, past the inflow orifice(s) 38, through the balloon 100, followed by additional transiting through the lumen 53 of the catheter tube 12a, through the strain relief tube 28, the tapered central passageway 58 (FIG. 3), slideably within and in sealed engagement with the hemostasis valve 66 (FIG. 3) to finally exit from the hemostasis nut 30.

The distal portion of the high pressure tube 50 delivers pressured saline or other suitable fluid to the fluid jet emanator 52a to produce and distribute non-hemolyzing radially directed fluid jet streams 92 of saline or other suitable fluids which emanate as direct stream from the radially directed jet orifices 90a-90n of the fluid jet emanator 52a to accomplish thrombectomy functions in a manner as previously described. Carefully generated operating pressure and fluid flows at values short of hemolysis can be accomplished primarily by controlling the input fluid pressure at the high pressure fluid pump 44 and/or by controlling the exhaust rate at the exhaust regulator 47, whereby the exhaust regulator 47 is operated to provide a negative pressure for effecting effluent aspiration. Additionally, the pressured saline, or other suitable fluid, is also delivered by the high pressure tube 50 to the fluid jet emanator 52a to produce and distribute proximally directed fluid jet streams 108 of saline or other suitable fluids which are directed proximally from the proximally directed jet orifices 106a-106n (FIG. 9) of the fluid jet emanator 52a, and to thence transit parallel to the inflow orifice(s) 38, and finally into the distal section of the catheter tube 12a to flow proximally therethrough and provide for the inflation of the balloon 100 and to complement the aspiration of effluent flow.

The balloon 100 is automatically and expandingly deployed to reform as an inflated balloon 100a by the pressure exerted from the proximally directed high velocity fluid jet streams 108 emanating from the proximally directed jet orifices 106a-106n of the fluid jet emanator 52a and complemented by the pressurized effluent flow through the lumen 53 of the catheter tube 12a. The pressurized inflation of the inflated balloon 100a or maintaining a state of inflation of the inflated balloon 100a is also assisted by utilizing back pressure along the length of the catheter tube 12a. An operational advantage of the present catheter system is the utilization of an exhaust outflow and an internal pressure which are produced by the proximally directed fluid jet stream(s) 108 in combination with a restrictive control of the outflow, such as influenced by the exhaust regulator 47 in assisting an automatic expansion of the balloon 100 which forcibly impinges upon and seals against the inner walls of the blood vessel 96. The reduced thickness of the material comprising the balloon 100 allows the balloon 100 to expand sufficiently to reform as the inflated balloon 100a, the further expansion of which is restricted by its impingement on the wall of the blood vessel 96. The operating pressure and fluid flows affecting the inflation of the balloon 100 can be affected primarily by controlling the input fluid pressure at the high pressure fluid pump 44 and/or by controlling the exhaust rate at the exhaust regulator 47 whereby the exhaust regulator 47 is operated to provide a negative pressure for effecting effluent aspiration. Other fluid jet emanators of appropriate size and/or configuration can also be incorporated in lieu of the fluid jet emanator 52a positioned within the distal section of the catheter tube 12a in order to emanate or emit one or more radially directed fluid jet streams 92 and to emanate or emit one or more proximally directed fluid jet streams 108 proximally along or near the longitudinal axis of the catheter tube 12a; the preceding alternatives shall not be considered to be limiting to the scope of the disclosure.

By inflating the balloon 100, the peripheral circumference of the inflated balloon 100a impinges upon the wall of the blood vessel 96 in order to effect a fluid flow reduction or cessation within the blood vessel 96. The inflated balloon 100a, i.e., the balloon 100, can be compliant, semi-compliant, or noncompliant according to the procedure performed. The inflated balloon 100a provides for the uniform centering and positioning of the distal section of the catheter tube 12a within the blood vessel 96, thereby providing a substantially equal annular spacing between the wall of the blood vessel 96 and the inflow orifice 38 for uniform access and clearance thereto and thereabout. The inflated balloon 100a also provides for an annular spacing between the blood vessel 96 and the inflow orifice(s) 38 in order to provide for the access and clearance to and about the inflow orifice 38.

The use of the radially directed fluid jet streams 92 from the radially directed jet orifices 90a-90n provides for the fluid jet impingement of the deposits of lesions or thrombus 98 on the inner wall of the blood vessel 96 adjacent to or in close proximity to the radially directed jet orifices 90a-90n in order to impinge, ablate and loosen deposits of lesions or thrombus 98, whereby such thrombus or lesion particulate and fluids can be entrained through one or more inflow orifices 38 by aspiration involving the use of the exhaust regulator 47, as previously described. The action and high velocity of the proximally directed fluid jet streams 108 of saline or other suitable fluids proximally through the catheter tube 12a, in addition to causing the inflation of balloon 100, provide a force for driving thrombus or lesions 98 and fluid flow proximally through the lumen 53 of the catheter tube 12a. As previously described, drugs for treatment or for lysing of the thrombus deposits or lesions 98 can also be delivered via the high pressure tube 50 and the fluid jet emanator 52a and the radially directed jet orifices 90a-90n and radially directed fluid jet streams 92 in order to soften the deposits of lesions or thrombus 98 in the region of the blood vessel 96 adjacent to or in close proximity to the radial jet orifices 90a-90n, thereby benefiting and making use of the radially directed fluid jet streams 92 more effective.

The proximally directed fluid jet streams 108 impinge upon, provide drag forces on, and break up or macerate such entrained thrombus or lesions 98 particulate and/or debris which have been ingested and entrained through the inflow orifice(s) 38. Such debris is further entrained, urged and carried proximally along the lumen 53 of the catheter tube 12a by internal pressure and by aspiration involving the exhaust regulator 47, as well as by the additional force provided by the action of the proximally directed fluid jet streams 108. The entrainment of thrombus or lesions 98 particulate and/or debris through the inflow orifice(s) 38 is influenced by and based on coordinated association primarily involving the operation of the exhaust regulator 47 and the operation of the high pressure fluid pump 44 through the catheter 12a. In such a catheter system, the inflow orifice 38 is sufficiently sized for aspiration or multiple inflow orifices may be used in order to achieve a desired fluid inflow and aspiration. The catheter tube 12a may be moved proximally or distally during the procedure to maximize the effect of the catheter system. The balloon 100 can be alternately pressurized and depressurized, whereby thrombus or lesions 98 can be compacted in order to enlarge a passage. When the procedure is complete, the inflated balloon 100a is generally deflated sufficiently under normal arterial pressure to be removed safely, or deflation can be aided with a manual syringe attached to the manifold, or deflation can be aided by means of the exhaust regulator 47. Further interventions can be executed as normal over the remaining guidewire or guidewire device. Cessation of fluid flow in a blood vessel or other conduit maximizes the effect of the catheter system 10a in terms of debris or tissue removal. Use of devices of the present disclosure can also provide for the performance of a modified embolectomy by breaking up clots as the inflated balloon 100a is moved through a blocked vessel or can be used to minimize any distal or proximal embolization.

In the present disclosure, the radially directed fluid jet streams 92 are driven by the same pressure source as the proximally directed fluid jet streams 108. The velocity of the fluid directed jet streams is controlled by the high pressure pump 44, the total area of all of the radially directed jet orifices 90a-90n and the proximally directed jet orifices 106a-106n. Debris removal is influenced by and accomplished by aspiration in coordination with the operation of the high pressure fluid pump 44 and the exhaust regulator 47 through the catheter tube 12a. In such a catheter system, the inflow orifice 38 is sufficiently sized for aspiration. By sizing the radially directed jet orifices 90a-90n and the proximally directed jet orifices 106a-106n and operating the high pressure pump 44 within suitable parameters, the velocity and strength of the radially directed fluid jet streams 92 and the proximally directed fluid jet streams 108 can be influenced and controlled. The use of nominally sized radially directed jet orifices 90a-90n provides for the use of fluid jet streams having enough momentum that can be delivered by large non-hemolysing fluid jet streams (92) which are equivalent in energy, via increased flow rate, to high velocity smaller fluid jet streams described later. The principle for an aggressive debris removal is based on the velocity of the radially directed jet streams 92. Consider that there is some critical velocity for debris liberation. As the radially directed fluid jet streams 92 travel through a fluid environment, the fluid jet streams will entrain surrounding fluid and the fluid jet streams will slow. There are empirical relationships for turbulent jet streams that show that velocity is proportional to the diameter of the jet streams and to the initial velocity of the jet streams. Thus, the velocity of the turbulent jet streams at a given distance could be increased by either increasing the initial fluid jet stream velocity or increasing the jet orifice diameters. Note that if the jet orifice diameters are increased, the high pressure pump rate of the pump 44 would need to be increased in order to maintain the fluid jet stream velocity. In practice, the present catheter system is designed with a given set of jet orifice diameters and with the high pressure pump 44 pump rate adjusted to achieve the proper efficacy.

Figure 11:
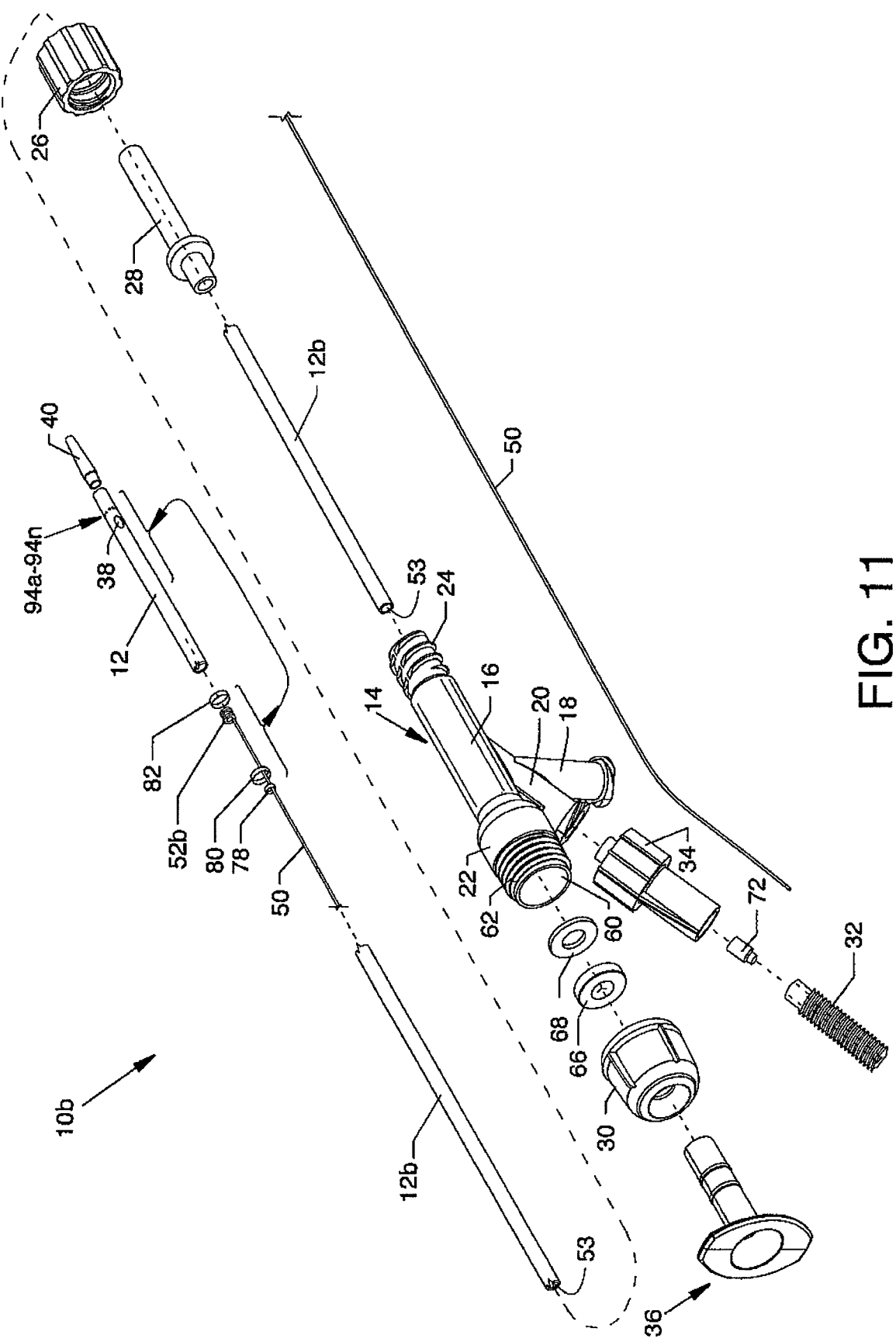
FIG. 11, a second alternative embodiment, is an isometric exploded and segmented view of a catheter tube and a manifold which are used with enabling components shown in FIG. 1.

FIG. 11, a second alternative embodiment is shown as an illustration similar in many respects to FIG. 2 showing a direct stream hydrodynamic catheter tube 12b, also referred to as the catheter tube 12b, and a manifold 14 and components associated therewith and wherein each is connected to and utilizes functions of the accompanying enabling components in a manner similar to that shown in FIG. 1 where all numerals correspond to those elements previously described or as otherwise described herein. The components of FIG. 11 are used with the enabling components referred to and shown in FIG. 1 where such enabling components consist of the high pressure fluid source 42, the high pressure fluid pump 44, the threaded high pressure connection port 32 and connector 46, the exhaust regulator 47, the collection chamber 48, and the connector 49 all which are used much in the same manner as previously described. Together, the referenced enabling components in combination with the catheter tube 12b and the manifold 14 and closely associated components thereof comprise a direct stream hydrodynamic catheter system 10b which is also referred to as the catheter system 10b. The catheter system 10b of this embodiment provides for an increased fluid velocity with smaller sized radially projected fluid jet streams therefrom by using smaller radially directed jet orifices, as well as including the provision of and the use of the previously described proximally directed fluid jet streams 108. Although the catheter tube 12b, the manifold 14, and closely associated components of each are shown referenced to the catheter system 10b in FIG. 11, it is understood that the previously referenced enabling components referred to and shown in FIG. 1, but not shown in FIG. 11, are also a significant part of the catheter system 10b.

Figure 12:
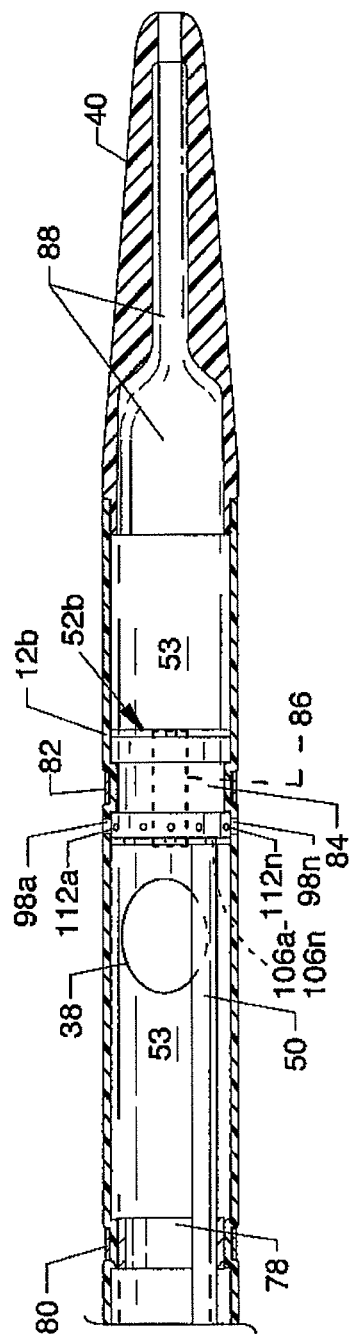
FIG. 12 is an illustration similar in many respects to FIG. 4 illustrating the distal portion of the catheter tube and the relationships of radiopaque marker bands, a support ring, a high pressure tube, and a fluid jet emanator to each other and to the catheter tube.
Figure 13:
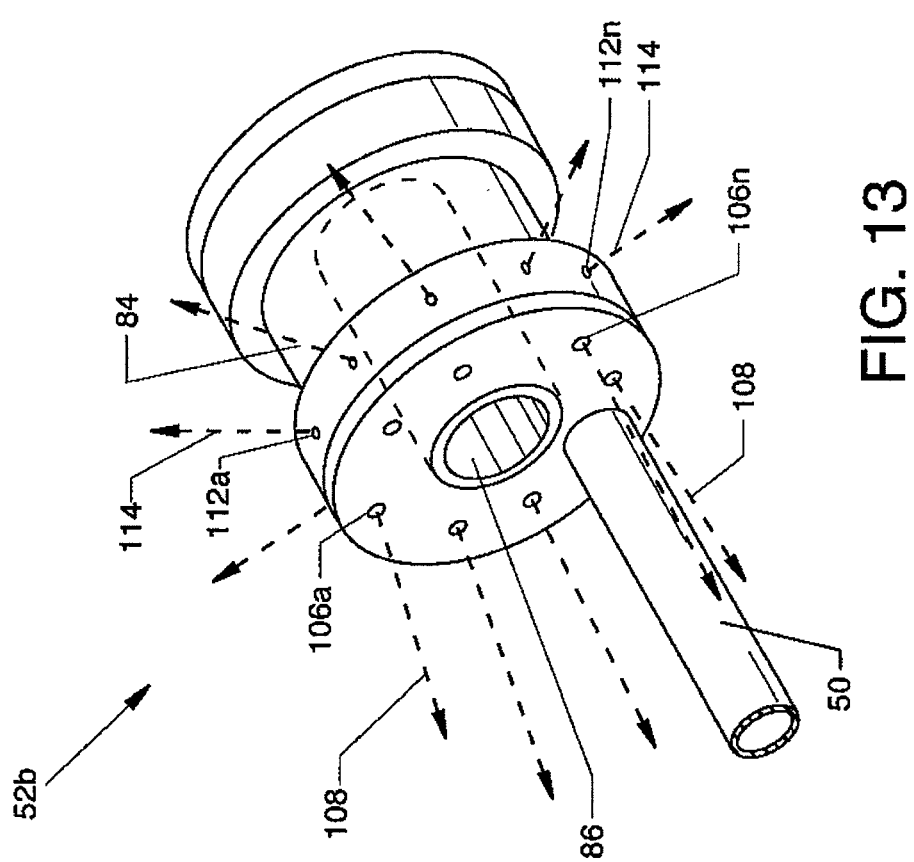
FIG. 13 is an illustration similar in many respects to FIG. 5 and is an isometric view of another fluid jet emanator shown connected to and in communication with a high pressure tube.

FIG. 12 is an illustration similar in many respects to FIG. 4 showing the distal end of the catheter tube 12b used in lieu of the catheter tube 12 and shown in use with a fluid jet emanator 52b in lieu of the fluid jet emanator 52, wherein the fluid jet emanator 52b includes additional structure, features and functionality such as described in FIG. 13.

FIG. 13 is an illustration similar in many respects to FIG. 9 showing an isometric view of the alternative fluid jet emanator 52b connected to and in communication with the high pressure tube 50 alternatively including the plurality of small sized radially directed jet orifices 112a-112n in lieu of the nominally sized radially directed jet orifices 90a-90n of the previous embodiments. The fluid jet emanator 52b also includes the previously shown and described plurality of proximally (rearwardly) directed orifices 106a-106n located on and about a proximal face of the fluid jet emanator 52b in parallel alignment with the longitudinal axis of the fluid jet emanator 52b, as well as including the previously described annular groove 84 and passageway 86. The plurality of radially directed jet orifices 112a-112n and the plurality of proximally directed orifices 106a-106n are in common and are pressurized in common by the pressurized saline provided through the high pressure tube 50.

The high pressure tube 50 delivers pressurized saline or other suitable fluid to the fluid jet emanator 52b for producing and distributing small sized radially directed fluid jet streams 114 at a high pressure which jet streams emanate from the radially directed jet orifices 112a-112n of the fluid jet emanator 52b to vigorously and more powerfully perform functions, as described herein. The fluid jet emanator 52b also produces and distributes pressurized proximally directed fluid jet streams 108 of saline or other suitable fluids which fluid jet streams are directed proximally from the proximally directed orifices 106a-106n to perform functions, as described herein.

Mode of Operation

Generally, a normal guidewire is deployed in a blood vessel 96 requiring treatment, or in the alternative, a filter guidewire or balloon occlusion guidewire could also be used. The catheter tube 12b and other closely associated and aligned components directly associated therewith consisting mainly of the high pressure tube 50 and the fluid jet emanator 52 are advanced over and along a guidewire (37) which is aligned within the blood vessel 96 for the purpose of debris/thrombus/lesion removal, drug infusion, or other procedures, and maneuvered into an appropriate position for treatment. A generic guide catheter or sheath can be incorporated as necessary to offer assistance in placing the catheter tube 12b and closely aligned components, in direct association therewith, of the direct stream hydrodynamic catheter system 10b within the desired location of the blood vessel 96 in order that the tapered tip 40 of the catheter tube 12b can be extended through and beyond the thrombus or lesions 98 and in order to position the fluid jet emanator in very close proximity to the thrombus or lesions 98. The direct stream thrombectomy catheter 10b is then activated wherein thrombus, debris, lesions and the like can be infused by a desired procedure. The catheter tube 12b may be moved proximally or distally during the procedure to maximize the effect of the system. Further interventions can be executed as normal over the remaining guidewire or guidewire device.

Figure 14:
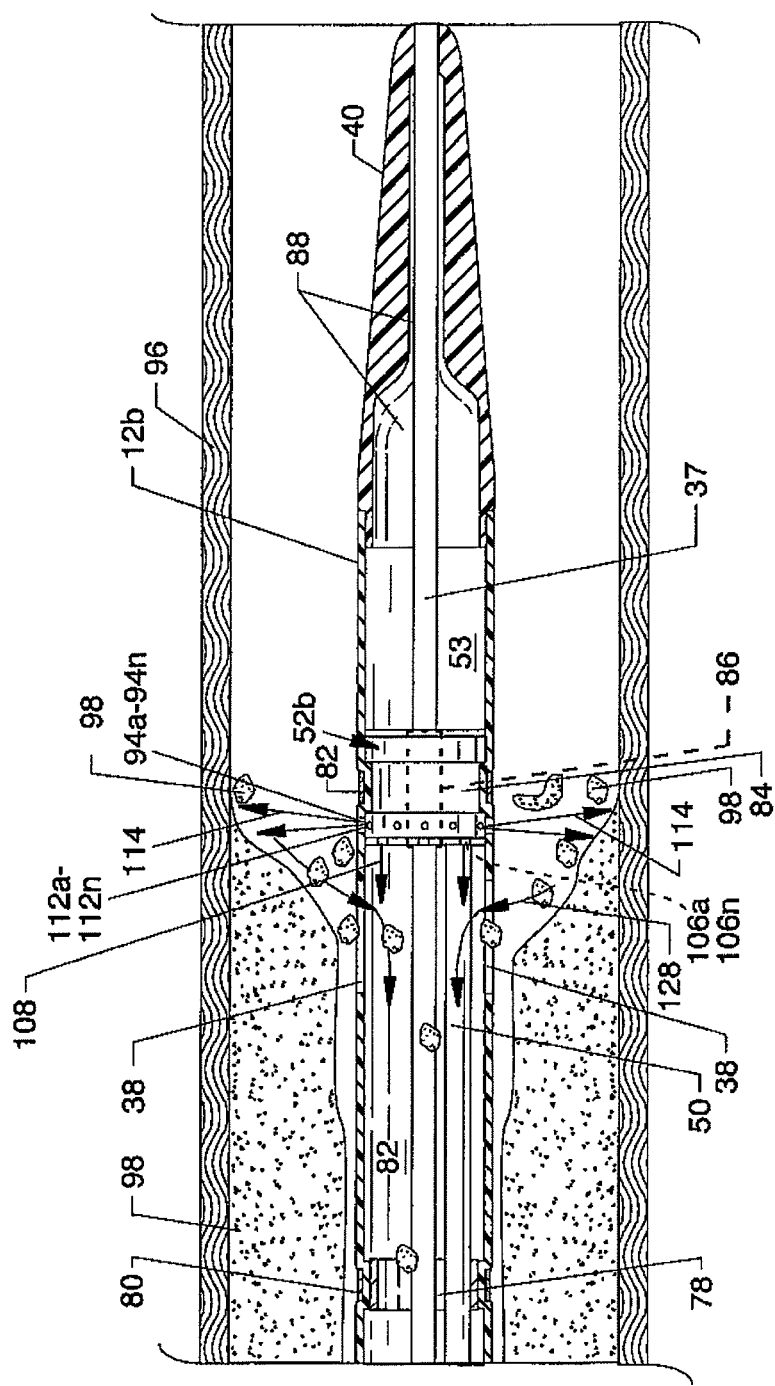
FIG. 14 is similar in many respects to FIG. 6 and is a side view, in partial cross section, of the distal portion of the catheter tube in the performance of the method and use thereof which performance utilizes enabling connections and which utilizes functions of the accompanying components in a manner as shown in FIG. 1.

Moreover, FIG. 14 is a side view, in partial cross section, of the catheter tube 12b of the second alternative embodiment illustrating the performance of the method and use thereof which utilizes enabling connections and which performance utilizes functions of the accompanying components in a manner similar to that shown in FIG. 1 with particular attention given to the distal section of the catheter tube 12b, the flexible tapered tip 40, the fluid jet emanator 52b, the inflow orifice(s) 38 (reoriented), and other closely associated components positioned in the blood vessel 96 containing deposits of thrombus or lesions 98. More specifically and with reference to FIGS. 1 and 14, the mode of operation is further described in use whereby the direct stream hydrodynamic catheter tube 12b is engaged over and about the guidewire 37 in a manner as previously described. The distal portion of the high pressure tube 50 delivers pressurized saline or other suitable fluid to the fluid jet emanator 52b to produce and distribute small sized, high powered, radially directed fluid jet streams 114 of saline or other suitable fluids which emanate as direct stream from the radially directed jet orifices 112a-112n of the fluid jet emanator 52b to accomplish thrombectomy functions, as previously described. Carefully generated operating pressure and fluid flows can be influenced primarily by controlling the input pressure fluid at the high pressure fluid pump 44 and/or by controlling the exhaust rate at the exhaust regulator 47, whereby the exhaust regulator 47 is operated to provide a negative pressure for effluent aspiration. Other fluid jet emanators of appropriate size and/or configuration can be incorporated in lieu of the fluid jet emanator 52b within the distal section of the catheter tube 12b in order to emanate or emit one or more radially directed fluid jet streams 114.

The use of the high powered radially directed fluid jet streams 114 from the radially directed jet orifices 112a-112n provides for the fluid jet impingement of the deposits of thrombus or lesions 98 on the inner wall of the blood vessel 96 adjacent to or in close proximity to the radially directed jet orifices 112a-112n in order to impinge, ablate and loosen deposits of thrombus or lesions 98, whereby such thrombus or lesion particulate and fluids can be entrained by the fluid inflow, as shown by the directed arrow 128 in FIG. 14, through one or more inflow orifices 38 by aspiration involving the use of the exhaust regulator 47 and exhausted proximally through the catheter tube 12b. Additionally, drugs for treatment or for lysing of the thrombus or lesions 98 can also be delivered via the radially directed jet orifices 112a-112n and radially directed fluid jet streams 114 in order to soften the deposits of thrombus or lesions 98 in the region of the blood vessel 96 adjacent to or in close proximity to the radial jet orifices 112a-112n, thereby making use of the radially directed fluid jet streams 114 more effective. The drugs are delivered through the high pressure tube 50 to the sites of the deposits of thrombus or lesions 98 using the fluid jet emanator 52b.

One or more inflow orifices 38 receive, ingest and entrain thrombus or lesions 98 in the form of particulate and/or debris therethrough by fluidic flow and are entrained to be urged and carried along the lumen 53 of the catheter tube 12b by aspiration involving the exhaust regulator 47, whereby the entrainment of thrombus or lesions 98 particulate and/or debris through the inflow orifice(s) 38 is influenced by and based on entrainment in association with aspiration in coordination with the exhaust regulator 47 through the catheter 12b. In such a device, the inflow orifice 38 is sufficiently sized for aspiration or multiple inflow orifices may be used in order to achieve a desired fluid inflow and aspiration. The outflow of fluid and thrombus or lesions is driven proximally through the catheter tube 12b by an internal pressure which results from the radially directed fluid jet streams 92 and the fluid entrained through the inflow orifice 38 and is assisted by aspiration by the use of the exhaust regulator 47.

In the present disclosure, the radially directed fluid jet streams 114 are driven by the same pressure source where the velocity is controllingly influenced by the high pressure pump 44 and the total area of all of the radially directed jet orifices 112a-112n. By sizing the radially directed jet orifices 112a-112n and operating the high pressure pump 44 within suitable parameters, the velocity and strength of the radially directed fluid jet streams 114 can be influenced and controlled. The principle for an aggressive debris removal is dependent on the velocity of the radially directed fluid jet streams 114. Consider that there is some critical velocity for debris liberation. As the radially directed fluid jet streams 114 travel through a fluid environment, the fluid jet streams will entrain surrounding fluid whereby the velocity of the fluid jet streams will slow. There are empirical relationships for turbulent fluid jet streams that show that velocity is proportional to the diameter of the fluid jet streams and to the initial velocity of the fluid jet streams. Thus, the velocity at a given distance could be increased by either increasing the initial fluid jet stream velocity or increasing the jet orifice diameter. As previously described, the pump flow rate must be adjusted depending on the size of the jet orifice diameter and the desired jet stream velocity.

Figure 15:
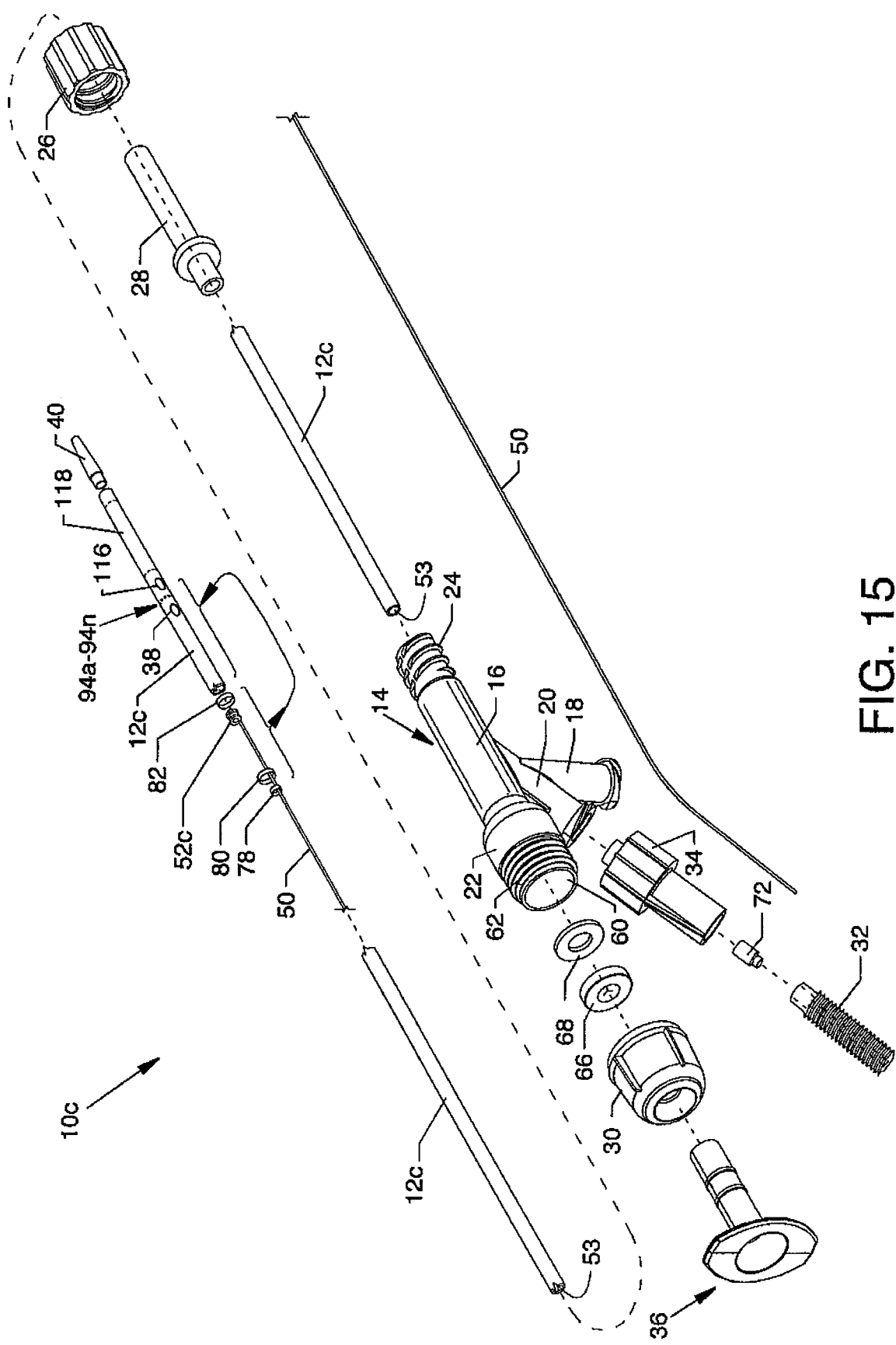
FIG. 15, a third alternative embodiment, is an isometric exploded and segmented view of a catheter tube and a manifold which are used with enabling components shown in FIG. 1.
Figure 16:
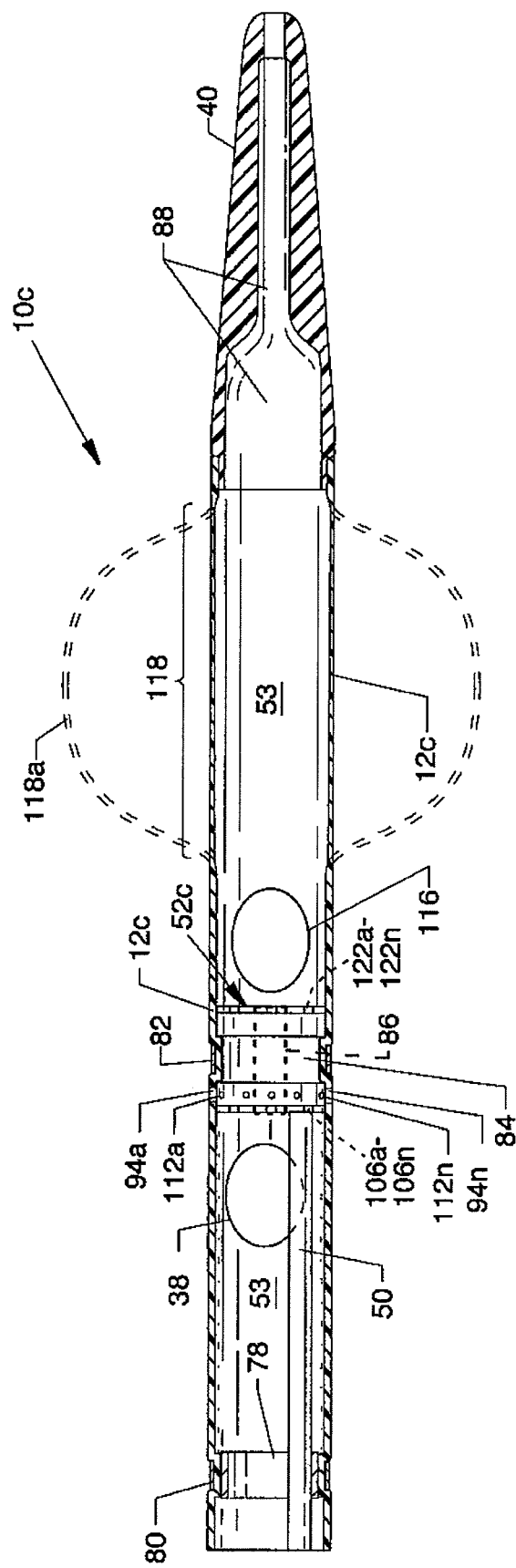
FIG. 16 is an illustration similar in many respects to FIG. 4 illustrating the distal portion of the catheter tube and the relationships of radiopaque marker bands, a support ring, a high pressure tube, a fluid jet emanator, and a balloon to each other and to the catheter tube.

FIG. 15, a third alternative embodiment, is an illustration similar in many respects to FIG. 2 showing a direct stream hydrodynamic catheter tube 12c, also referred to as the catheter tube 12c, and the manifold 14 and components associated therewith and wherein each is connected to and utilizes functions of the accompanying enabling components in a manner similar to that shown in FIG. 1 where all numerals correspond to those elements previously described or as otherwise described herein. The catheter tube 12 is reconfigured as a catheter tube 12c to additionally include one or more balloon inflation inflow orifices 116 located distal to a fluid jet emanator 52c, as best shown in FIG. 16, and a balloon 118 which is self-inflating and located at the distal end of the balloon inflation inflow orifice 116. The components of FIG. 15 are used with the enabling components referred to and shown in FIG. 1 where such enabling components consist of the high pressure fluid source 42, the high pressure fluid pump 44, the threaded high pressure connection port 32 and connector 46, the exhaust regulator 47, the collection chamber 48, and the connector 49 which are used much in the same manner as previously described. Together, the referenced enabling components in combination with the catheter tube 12c and the manifold 14 and closely associated components thereof comprise a direct stream hydrodynamic catheter system 10c which is also referred to as the catheter system 10c, wherein the catheter system 10c provides for an increased velocity but smaller sized radially projected fluid jet streams therefrom by using small sized radially directed jet orifices. The catheter system 10c includes the provision of and the use of the previously described pressurized proximally directed fluid jet streams 108 and the previously described pressurized radially directed fluid jet streams 114. Additionally, the catheter system 10c includes the provision of and the use of pressurized distally directed fluid jet streams 126 which emanate from the fluid jet emanator 52c (FIG. 17) for the inflation of the distally located balloon 118 in cooperation with the balloon inflation inflow orifice 116. Although the catheter tube 12c, the manifold 14, and closely associated components of each are shown referenced to the catheter system 10c in FIG. 15, it is understood that the previously referenced enabling components referred to and shown in FIG. 1, but not shown in FIG. 15, are also part of catheter system 10c.

Figure 17:
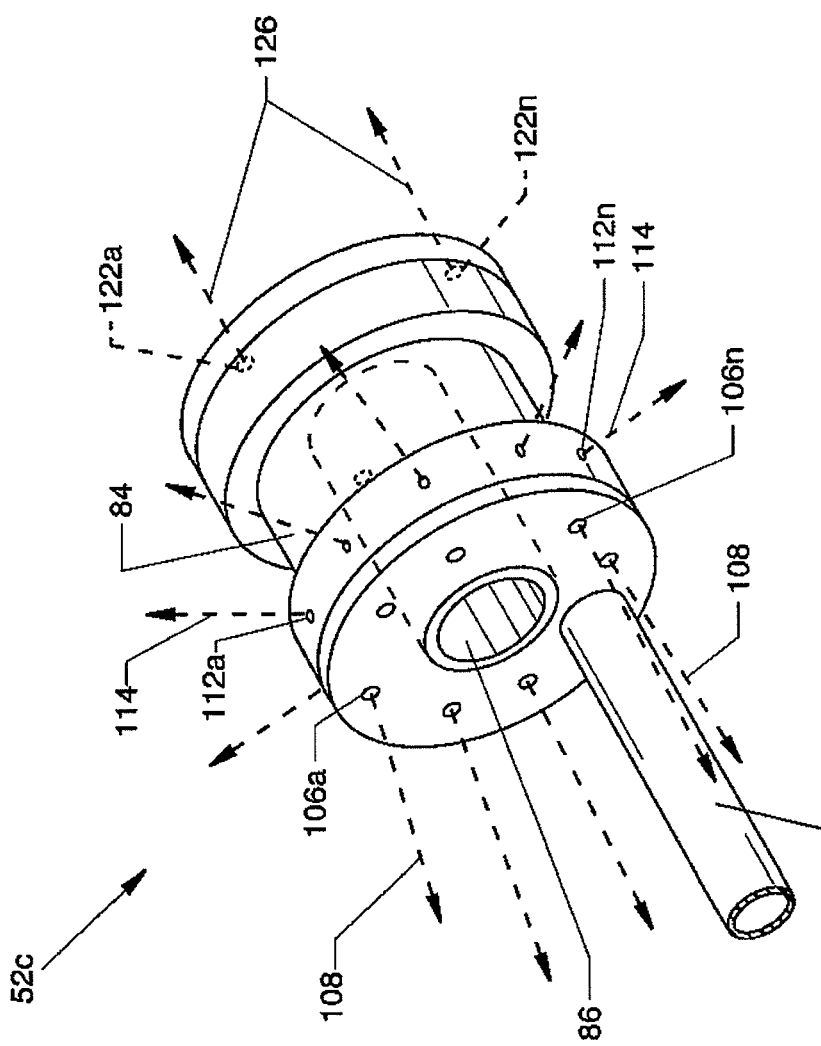
FIG. 17 is an illustration similar in many respects to FIG. 13 and is an isometric view of another fluid jet emanator shown connected to and in communication with a high pressure tube.

FIG. 16 is similar in many respects to FIG. 4 illustrating the distal end of a catheter tube 12c reconfigured and used in lieu of the catheter tube 12 and shown in use with the fluid jet emanator 52c in lieu of the fluid jet emanator 52, wherein the fluid jet emanator 52c includes additional structure, features and functionality such as described for FIG. 17. Shown more specifically is the relationship and arrangement of the inflow orifice 38 (reoriented), the proximally directed jet orifices 106a-106n of the fluid jet emanator 52c, the radially directed jet orifices 112a-112n of the fluid jet emanator 52c, the distally directed jet orifices 122a-122n of the fluid jet emanator 52c, the balloon inflation inflow orifice(s) 116 (reoriented) and the self-inflating balloon 118. Also shown is the plurality of holes 94a-94n extending through the wall of the catheter tube 12c in corresponding alignment with the radially directed jet orifices 112a-112n. High velocity radially directed fluid jet streams 114 (FIG. 17) emanate through the radially directed jet orifices 112a-112n and through the plurality of holes 94a-94n of the catheter tube 12c in order to provide treatment as shown and described in FIG. 18. The balloon 118 which is continuous with the catheter tube 12c, preferably has a wall thickness less than that of the general wall thickness of the catheter tube 12c, is generally aligned in longitudinal orientation along the catheter tube 12c between the balloon inflation inflow orifice 116 and the tapered flexible tip 40. The profile of the balloon 118 in the inflated mode is shown in dashed lines and referenced as the inflated balloon 118a.

FIG. 17 is an illustration similar in many respects to FIG. 13 showing an isometric view of the alternative fluid jet emanator 52c connected to and in communication with the high pressure tube 50. A plurality of distally (forwardly) directed jet orifices 122a-122n is additionally located on and about the distal face of the fluid jet emanator 52c. As previously shown and described, the plurality of small sized radially directed jet orifices 112a-112n is also included about the periphery of the fluid jet emanator 52c. The fluid jet emanator 52c also includes the plurality of proximally (rearwardly) directed jet orifices 106a-106n located on and about the proximal face of the fluid jet emanator 52c, as well as including the previously described annular groove 84 and passageway 86. The plurality of radially directed jet orifices 112a-112n, the plurality of proximally directed orifices 106a-106n and the plurality of distally directed jet orifices 122a-122n are in common and are pressurized in common by pressurized saline provided through the high pressure tube 50.

Figure 18:
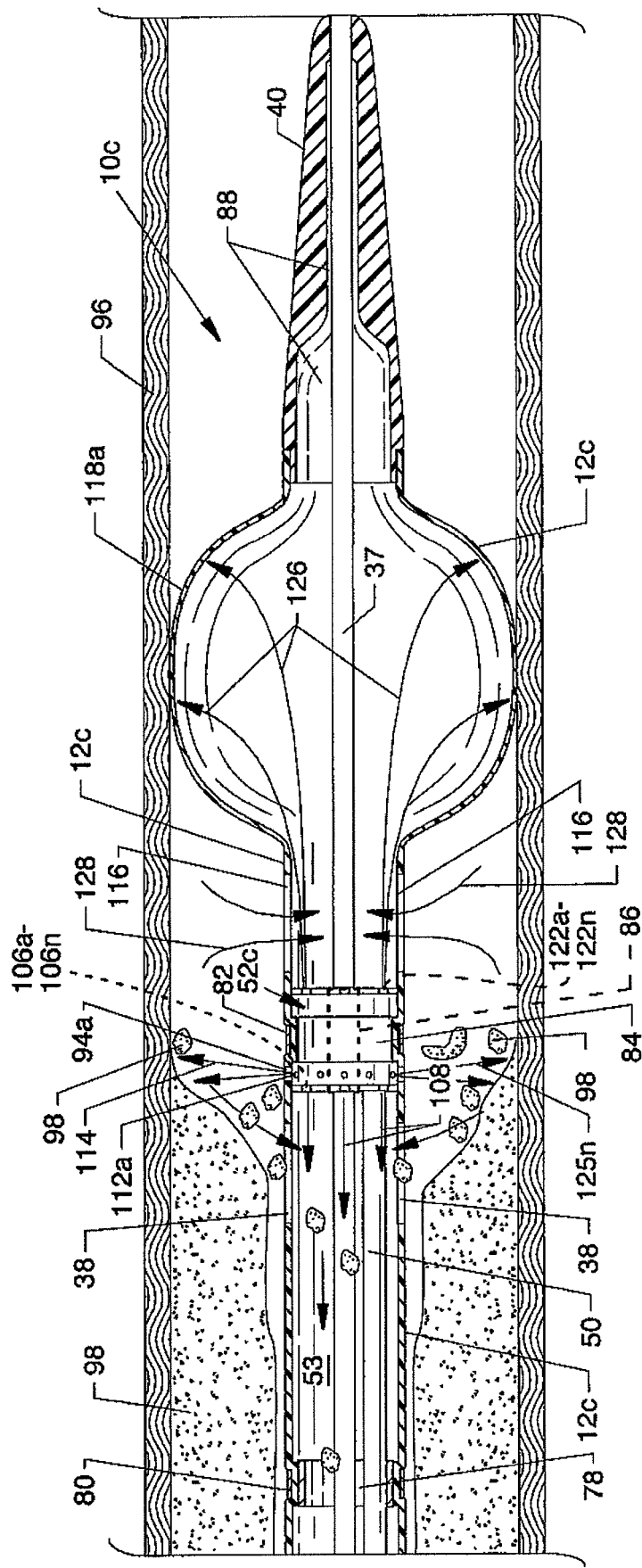
FIG. 18 is similar in many respects to FIG. 6 and is a side view, in partial cross section, of the distal portion of the catheter tube in the performance of the method and use thereof which performance utilizes enabling connections and which utilizes functions of the accompanying components in a manner as shown in FIG. 1.

The high pressure tube 50 delivers pressurized saline or other suitable fluids to the fluid jet emanator 52c to produce and distribute high pressure distally directed fluid jet streams 126 which emanate from the distally directed jet orifices 122a-122n in order to provide for the automatic pressurization and inflation of the balloon 118 as shown in FIG. 18. In a manner as previously described, the high pressure tube 50 delivers pressurized saline or other suitable fluid to the fluid jet emanator 52c for producing and distributing high velocity but small sized radially directed fluid jet streams 114 of saline or other suitable fluids which emanate from the radially directed jet orifices 112a-112n of the fluid jet emanator 52c to vigorously and more powerfully perform functions, as described herein. As previously described, the fluid jet emanator 52c also produces and distributes pressurized proximally directed fluid jet streams 108 of saline or other suitable fluids which are directed proximally from the proximally directed orifices 106a-106n to perform functions, as described herein.

Mode of Operation

In a closely related manner as previously described herein and with reference to FIG. 18, the method of operation of a third alternative embodiment is now described. Generally, a normal guidewire 37 is deployed in a blood vessel 96 requiring treatment. The catheter tube 12c and other closely associated and aligned components directly associated therewith consisting mainly of the high pressure tube 50, the fluid jet emanator 52c, the distal section of the catheter tube 12c, and the uninflated balloon 118 are advanced over and along the guidewire (37) and aligned within the blood vessel 96 for the purpose of cell harvesting, debris/thrombus/lesion maceration or removal, drug infusion, or other procedures; the catheter tube is maneuvered into an appropriate position within the blood vessel 96 for treatment. A generic guide catheter or sheath can be incorporated as necessary to offer assistance in placing the catheter tube 12c and closely aligned components in direct association therewith of the direct stream hydrodynamic catheter system 10c within the desired location of the blood vessel 96 in order that the tapered flexible tip 40 of the catheter tube 12c can be extended through the thrombus or lesions 98 to a position where the fluid jet emanator 52c is in very close proximity to the thrombus or lesions 98 and where the self-inflating balloon 118 is distal to the thrombus or lesions 98. The direct stream thrombectomy catheter system 10c is then activated, whereby the balloon 118 is automatically and expandingly deployed reforming as an expanded balloon 118a, and then cell from the thrombus or vessel, debris and the like can be harvested (removed) by aspiration or by liquid flows directed proximally along the lumen 53 of the catheter tube 12c and subsequently spun in a separation centrifuge for sampling or drugs can be infused by a desired procedure.

Moreover, FIG. 18 is a side view, in partial cross section, of the catheter tube 12c of the third alternative embodiment of the present disclosure illustrating the performance of the method and use thereof which utilizes enabling connections and which utilizes functions of the accompanying components in a manner similar to that shown in FIG. 1 with particular attention given to the distal section of the catheter tube 12c, the flexible tapered tip 40, the inflated self-inflated balloon 118(a), the balloon inflation inflow orifice(s) 116 (reoriented), the fluid jet emanator 52c, the inflow orifice(s) 38, and other closely associated components positioned in the blood vessel 96 containing deposits of thrombus or lesions 98. For purposes of example and illustration, one or more inflow orifice(s) 38 (reoriented) are shown at the top and the bottom of the catheter tube 12c.

More specifically and with reference to FIG. 18, the mode of operation is further described. The distal portion of the high pressure tube 50 delivers pressured saline or other suitable fluid to the fluid jet emanator 52c to produce and distribute radially directed fluid jet streams 114 of saline or other suitable fluids which emanate as direct fluid jet streams from the radially directed jet orifices 112a-112n of the fluid jet emanator 52c to accomplish thrombectomy functions in a manner as previously described. Pressured saline, or other suitable fluid, is also delivered by the high pressure tube 50 to the fluid jet emanator 52c to produce and distribute proximally directed fluid jet streams 108 of saline or other suitable fluids which are directed proximally from the proximally directed jet orifices 106a-106n (FIG. 17) of the fluid jet emanator 52c, and to thence transit parallel to the inflow orifice(s) 38, and finally into the distal section of the catheter tube 12c to flow proximally therethrough in a manner as previously described. Additionally and with particular reference to this third alternative embodiment, pressurized saline or other suitable fluid is also delivered by the high pressure tube 50 to the fluid jet emanator 52c to produce and distribute distally directed fluid jet streams 126 of saline or other suitable fluids which are directed distally from the distally directed jet orifices 122a-122n (FIG. 17) in order to assist in the inflation of the balloon 118.

The distally directed fluid jet streams 126 of saline or other suitable fluids which are directed distally from the orifices 122a-122n (FIG. 17) of the fluid jet emanator 52c within and along the distal section of the catheter tube 12c in close proximity to the balloon inflation inflow orifice 116 and thence within the confines of the self-inflating balloon 118 result in the inflation of balloon 118a for the purposes of, but not limited to, impeding fluid flow within the blood vessel 96 to effect a stagnate fluid flow in the thrombus region, to provide centering of the distal section of the catheter tube 12c, and to assist in the accomplishment of thrombectomy functions, as described herein.

The self-inflating balloon 118 is automatically and expandingly deployed to reform as an inflated balloon 118a primarily by the pressure of the distally directed fluid jet streams 126 emanating from the jet orifices 122a-122n of the fluid jet emanator 52c. The fluid entrainment inflow, shown by the directed arrows 128 in FIG. 18 assists in the inflation of the self-inflating balloon 118. Pressurized inflation of the inflated balloon 118a or maintaining a state of inflation is also assisted by utilizing back pressure along the length of the catheter tube 12c. An operational advantage of this third alternative embodiment is the utilization of the exhaust outflow and internal pressure which is produced by the proximally directed fluid jet stream(s) 108 in combination with the restriction of the outflow, such as caused by the exhaust regulator 47, to assist in the automatic expansion of the balloon 118 which expanded balloon 118a forcibly impinges upon and seals against the inner wall of the blood vessel 96. The reduced thickness of the material comprising the balloon 118 allows the balloon 118 to expand sufficiently to become an inflated balloon 118a restricted by its impingement upon the wall of the blood vessel 96. The inflation pressure and fluid flows can be influenced by controlling the input fluid pressure at the high pressure fluid source 42 and/or by controlling the exhaust rate at the exhaust regulator 47. Other fluid jet emanators of appropriate size and/or configuration can be incorporated in lieu of the fluid jet emanator 52c within the proximal end of the distal section of the catheter tube 12c in order to emanate or emit one or more distally directed fluid jet streams 126, to emanate or emit one or more proximally directed fluid jet streams 108 along or near the longitudinal axis of the catheter tube 12c, and to emanate or emit one or more radially directed fluid jet streams 114 therefrom.

Inflation of the balloon 118 to form the inflated balloon 118a positions the peripheral circumference of the inflated balloon 118 against the wall of the blood vessel 96 in order to effect a fluid flow reduction or cessation within the blood vessel 96. The inflated balloon 118a, i.e., the balloon 118, can be compliant, semi-compliant, or noncompliant according to the procedure performed. The inflated balloon 118a provides uniform centering and positioning of the distal section of the catheter tube 12c within the blood vessel 96, thereby providing a substantially equal annular spacing between the wall of the blood vessel 96 and the inflow orifice 38 for uniform access and clearance thereto and thereabout. The inflated balloon 118a also provides for an annular spacing between the blood vessel 96 and the balloon inflation inflow orifice 116 in order to provide access and clearance to and about the balloon inflation inflow orifice 116.

The proximally directed fluid jet streams 108 provide a low pressure region at the inflow orifice 38 to ingest and entrain thrombotic particulate and/or debris 98 therethrough to impinge upon, provide drag forces on, and break up or macerate thrombotic particulate and/or debris 98, and by entrainment to urge and carry along one or more particles of thrombotic particulate and/or debris or lesion particulate 98 along the lumen 53 of the catheter tube 12c by the action of the proximally directed fluid jet streams 108. The entrainment of thrombotic particulate and/or debris 98 through the inflow orifice 38 is dependent on the high velocity fluid jet streams 108. The outflow of fluid and thrombus is generally driven proximally through the catheter tube 12c by an internal pressure which is produced by the high velocity fluid jet streams 108 and the fluid entrained through the inflow orifice 38 but also uses the assistance of fluid pressure forces provided by the radially directed fluid jet streams 114, the distally directed fluid jet streams 126 and assistance provided by aspiration.

The balloon 118 can be alternately pressurized and depressurized whereby the thrombus or lesions 98 can be compacted in order to enlarge a passage through the blood vessel 96. The catheter tube 12c may be moved proximally or distally during the procedure to maximize the effect of the catheter system. When the procedure is complete, the inflated balloon 118a is generally deflated sufficiently under normal arterial pressure so that the balloon 118 can be removed safely, or deflation of the balloon 118 can be aided with a manual syringe attached to the manifold, or deflation of the balloon 118 can be aided by means of the exhaust regulator 47. Other known interventions can be executed over the remaining guidewire or guidewire device. Cessation of fluid flow in a blood vessel or other conduit maximizes the effect of the catheter system 10c in terms of debris or tissue removal. Use of devices of the present disclosure can also provide for the performance of a modified embolectomy by breaking up clots as the inflated balloon 118a is moved through a blocked vessel or can be used to minimize any distal or proximal embolization.

In this alternative embodiment the radially directed fluid jet streams 114, the proximally directed fluid jet streams 108 and the distally directed fluid jet streams 126 are driven by the same fluid pressure. The velocity of the fluid jet streams is controllingly influenced by the high pressure pump 44 and the total area of all of the radially directed jet orifices 112a-112n, the proximally directed jet orifices 106a-106n and the distally directed jet orifices 122a-122n. Debris and sample removal are influenced by and assisted by aspiration in coordination with the operation of the high pressure fluid pump 44 and the exhaust regulator 47 which simultaneously introduces pressurized radially, proximally and distally directed fluid jet streams into the distal end of the catheter tube 12c. In such a catheter system, the inflow orifice 38 is sufficiently sized for aspiration to be effected. By sizing the radially directed jet orifices 112a-112n, the proximally directed jet orifices 106a-106n, the distally directed orifices 122a-122n and by operating the high pressure pump 44 within suitable parameters, the velocity and strength of the radially directed fluid jet streams 114, the proximally directed fluid jet streams 108 and the distally directed fluid jet streams 126 can be influenced and controlled. The principle for aggressive debris removal is dependent upon the velocity of the radially directed fluid jet streams 114. Consider that there is some critical velocity for debris liberation. As the radially directed fluid jet streams 114 travel through a fluid environment the fluid jet streams will entrain surrounding fluid whereby the fluid jet streams will slow. There are empirical relationships for turbulent jet streams that show that the velocity of the fluid jet streams is proportional to the diameter of the jet streams and to the initial velocity of the fluid jet streams. Thus, the velocity of the fluid jet streams, at a given distance, could be increased by either increasing the initial fluid jet stream velocity or increasing the jet orifice diameter. Note that if the jet orifice diameters are increased the high pressure pump 44 pump rate would need to be increased to maintain the fluid jet stream velocity. In practice, the catheter system is designed with a given set of jet orifice diameters and the high pressure pump 44 pump rate is adjusted to achieve the proper efficacy. In cases where cell sampling is desired, the velocity of the radially directed fluid jet streams 114 can be increased sufficiently to liberate microscopic rafts of cell clumps. The use of the distally located occlusion balloon 118a is helpful in ensuring that the liberated conduit cells do not migrate to distal vascular beds. For example, if the cells were cancerous ureter epithelial cells, the balloon 118a would minimize the chance for metastasizing.

Figure 19:
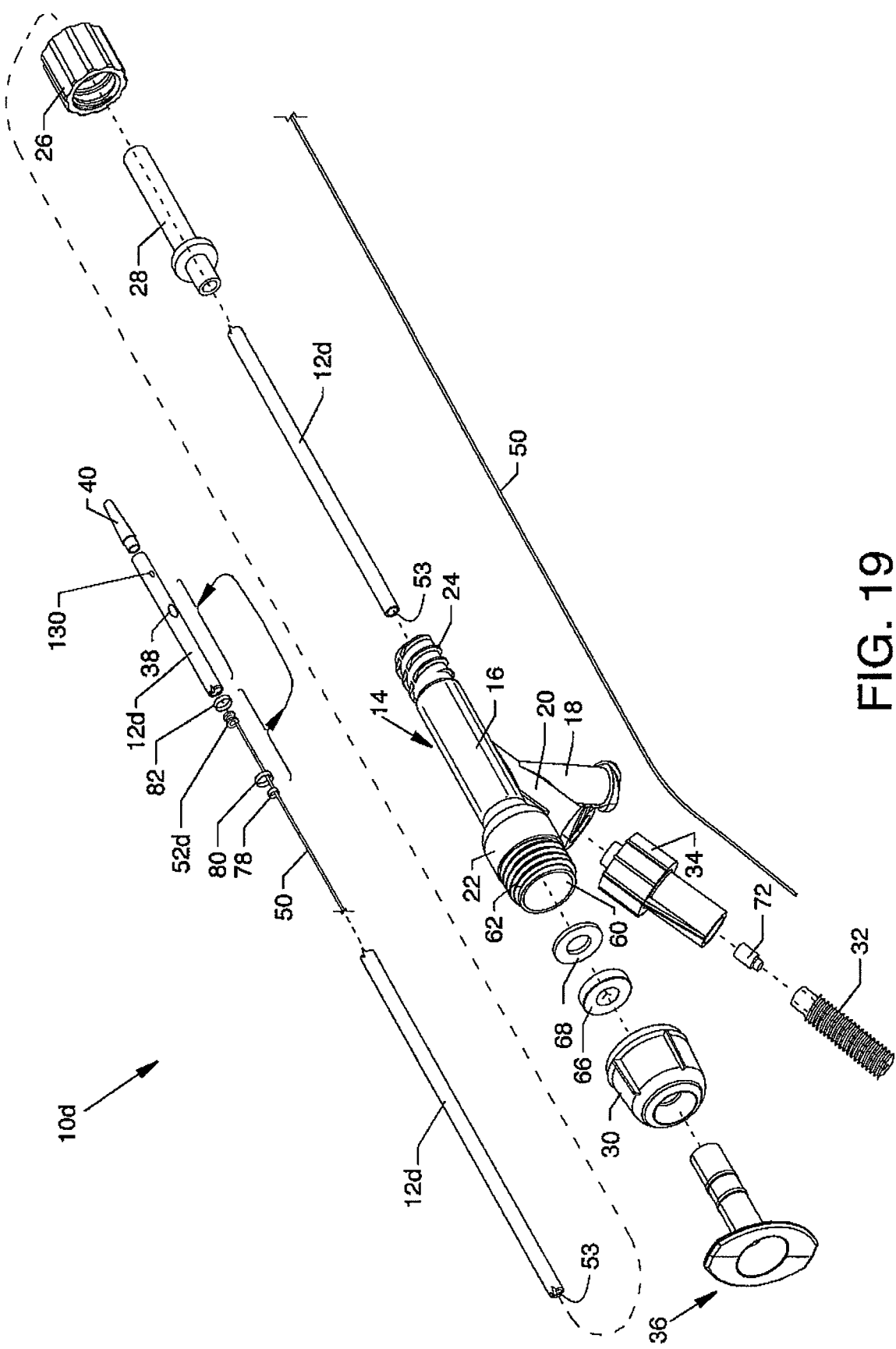
FIG. 19, a fourth alternative embodiment, is an isometric exploded and segmented view of a catheter tube and a manifold which are used with enabling components shown in FIG. 1.
Figure 20:
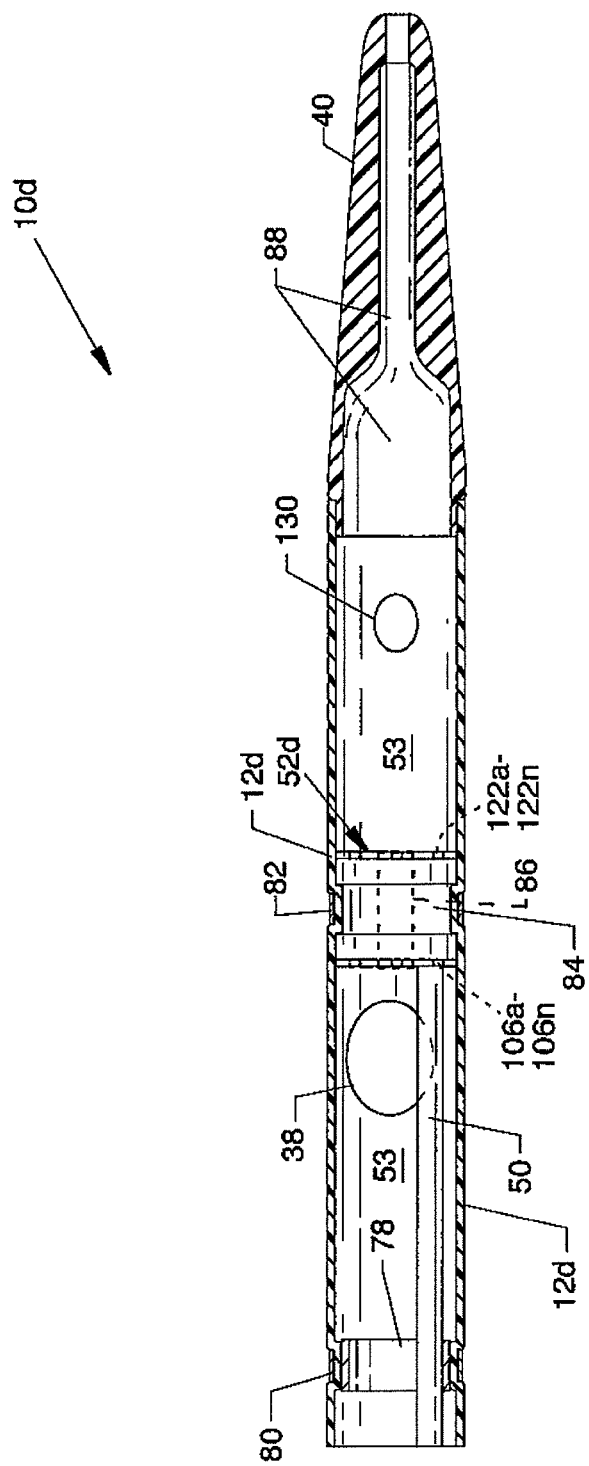
FIG. 20 is an illustration similar in many respects to FIG. 4 illustrating the distal portion of the catheter tube and the relationships of radiopaque marker bands, a support ring, a high pressure tube, and a fluid jet emanator to each other and to the catheter tube.

FIG. 19, a fourth alternative, is an illustration similar in many respects to FIG. 2 showing a direct stream hydrodynamic catheter tube 12d, also referred to as the catheter tube 12d, and the manifold 14 and components associated therewith and wherein each is connected to and which utilizes functions of the accompanying enabling components in a manner similar to that shown in FIG. 1 where all numerals correspond to those elements previously described or as otherwise described herein. The catheter tube 12 is reconfigured as a catheter tube 12d to additionally include one or more outflow orifice(s) 130 located in the distal portion of the catheter tube 12d at a location distal to a fluid jet emanator 52d, as best shown in FIG. 20. The outflow orifices 130 are utilized to provide low power direct streams in the form of cross stream jets 132 referenced in FIG. 22. The radially directed jet orifices 112a-112n and the radially directed fluid jet streams 114 are not utilized in this alternative embodiment. The components of FIG. 19 are used with the enabling components referred to and shown in FIG. 1 where such enabling components consist of the high pressure fluid source 42, the high pressure fluid pump 44, the threaded high pressure connection port 32 and connector 46, the exhaust regulator 47, the collection chamber 48, and the connector 49 which are used in much the same manner as previously described. Together, the referenced enabling components in combination with the catheter tube 12d and the manifold 14 and closely associated components thereof comprise a direct stream hydrodynamic catheter system 10d which is also referred to as the catheter system 10d, wherein the catheter system 10d provides for the use of a decreased velocity but large sized cross stream jets 132 therefrom by using outflow orifice(s) 130. The catheter system 10d includes the provision of and the use of the previously described pressurized proximally directed fluid jet streams 108 and the pressurized distally directed fluid jet streams 126 which emanate from the fluid jet emanator 52d (FIG. 21), whereby the distally directed fluid jet streams 126 pass through and emerge from the outflow orifice(s) 130 as newly featured low powered cross stream jets 132 (FIG. 22) to re-enter the catheter tube 12d at the inflow orifice 38. Although the catheter tube 12d, the manifold 14, and closely associated components of each are shown referenced to the catheter system 10d in FIG. 19, it is understood that the previously referenced enabling components referred to and shown in FIG. 1, but not shown in FIG. 19, are also part of the catheter system 10d.

Figure 21:
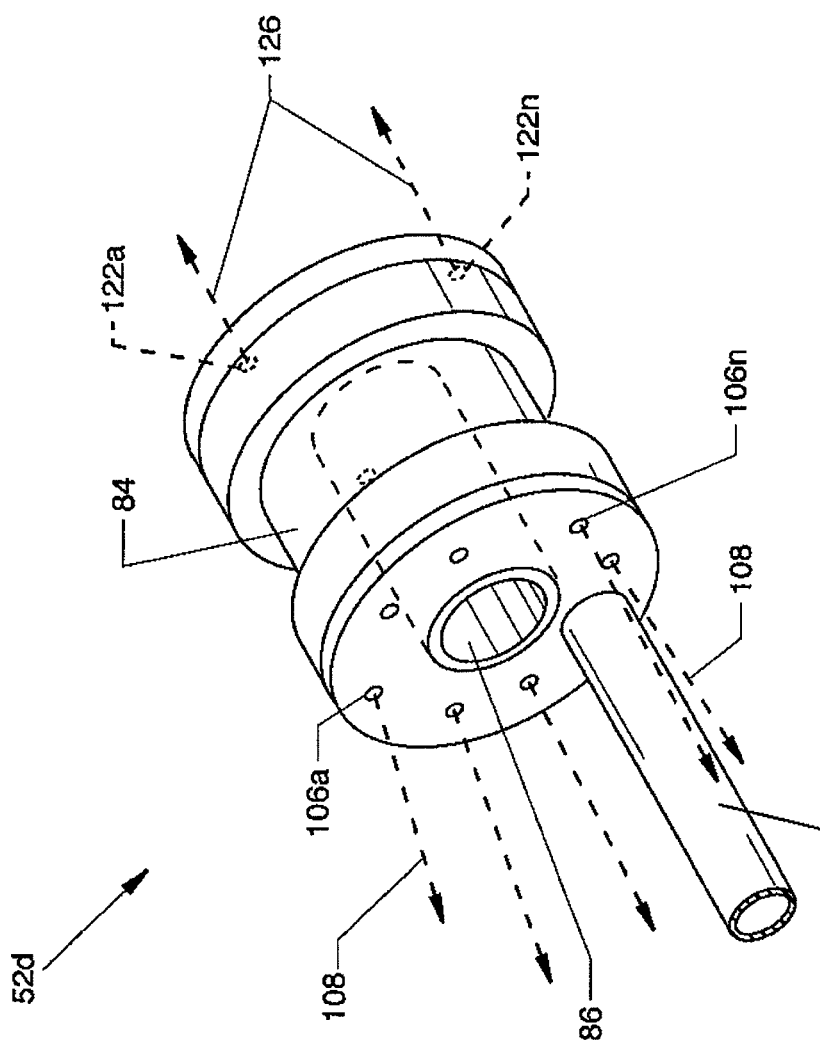
FIG. 21 is an illustration similar in many respects to FIG. 5 and is an isometric view of another fluid jet emanator shown connected to and in communication with a high pressure tube.

FIG. 20 is an illustration similar in many respects to FIG. 4 showing the distal end of a catheter tube 12d reconfigured and used in lieu of the catheter tube 12 and shown in use with the fluid jet emanator 52d in lieu of the fluid jet emanator 52, wherein the fluid jet emanator 52d includes many of the structural features and much of the functionality such as described for FIG. 21. Shown more specifically is the relationship and arrangement of the inflow orifice 38 (reoriented), the proximally directed jet orifices 106a-106n of the fluid jet emanator 52d, the distally directed jet orifices 122a-122n of the fluid jet emanator 52d and the outflow orifice(s) 130. The plurality of radially directed jet orifices 112a-112n for the emanation of radially directed jet streams 114 is not included in the fluid jet emanator 52d and the plurality of holes 94a-94n of the previously shown catheter tubes 12a-12c is not included in the catheter tube 12d.

FIG. 21 is an illustration similar in many respects to FIG. 17 showing an isometric view of the alternative fluid jet emanator 52d connected to and in communication with the high pressure tube 50. As previously described, the plurality of distally (forwardly) directed jet orifices 122a-122n is located on and about the distal face of the fluid jet emanator 52d. Also included are the previously shown and described plurality of proximally (rearwardly) directed jet orifices 106a-106n located on and about the proximal face of the fluid jet emanator 52d. The fluid jet emanator 52d also includes the previously described annular groove 84 and passageway 86. The plurality of proximally directed orifices 106a-106n and the plurality of distally directed jet orifices 122a-122n are in common and are pressurized in common by pressurized saline provided through the high pressure tube 50.

Figure 22:
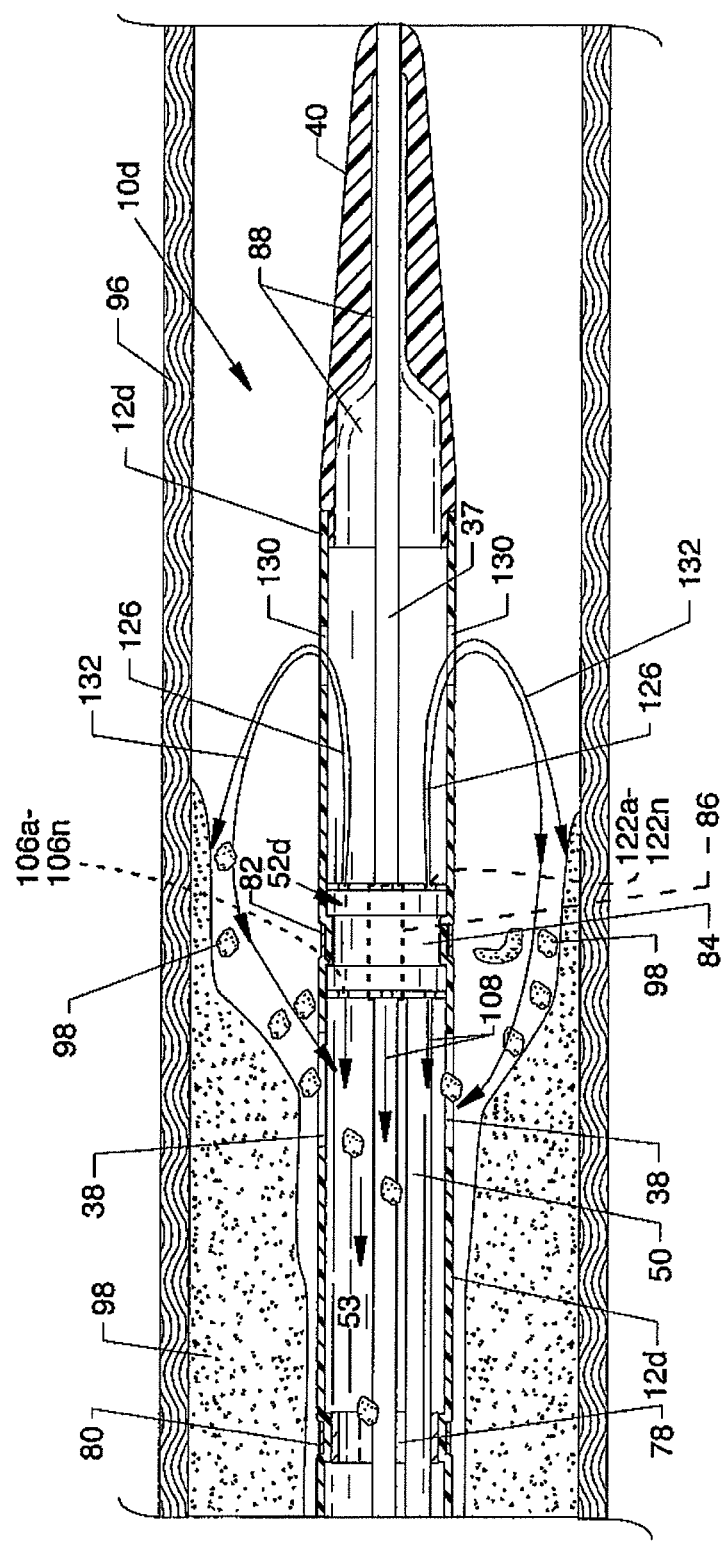
FIG. 22 is similar in many respects to FIG. 6 and is a side view, in partial cross section, of the distal portion of the catheter tube in the performance of the method and use thereof which performance utilizes enabling connections and which utilizes functions of the accompanying components in a manner as shown in FIG. 1.

The high pressure tube 50 delivers high pressure saline or other suitable fluids to the fluid jet emanator 52d to produce and distribute pressurized distally directed fluid jet streams 126 which emanate from the distally directed jet orifices 122a-122n in order to provide for the generation of cross stream jets 132 used for thrombus or lesion treatment (FIG. 22). In a manner as previously described, the high pressure tube 50 delivers pressurized saline or other suitable fluid to the fluid jet emanator 52d for producing and distributing pressurized proximally directed fluid jet streams 108 of saline or other suitable fluids which fluid jet streams are directed proximally from the proximally directed orifices 106a-106n to perform functions, as described herein.

Mode of Operation

In a closely related fashion and manner as previously described herein and with reference to FIG. 22, the method of operation of the fourth alternative embodiment is now described. Generally, a normal guidewire 37 is deployed in a blood vessel 96 requiring treatment, or in the alternative, a filter guidewire or balloon occlusion guidewire could also be used. The catheter tube 12d and other closely associated and aligned components directly associated therewith consisting mainly of the high pressure tube 50, the fluid jet emanator 52d and the distal section of the catheter tube 12d are advanced over and along the guidewire (37) and aligned within the blood vessel 96 for the purpose of debris/thrombus/lesion maceration or removal, drug infusion, or other procedures; the catheter tube is maneuvered into an appropriate position within the blood vessel 96 for treatment. A generic guide catheter or sheath can be incorporated as necessary to offer assistance in placing the catheter tube 12d and closely aligned components in direct association therewith of the direct stream hydrodynamic catheter system 10d within the desired location of the blood vessel 96 in order that the tapered flexible tip 40 of the catheter tube 12d can be extended through the thrombus or lesions 98 to a position where the fluid jet emanator 52d is in very close proximity to the thrombus or lesions 98. The direct stream thrombectomy catheter system 10d is then activated, whereby thrombus, debris and the like can be removed by action of the cross stream jet(s) 132 preferably in association with other methods previously described or drugs can be infused by a desired procedure.

Moreover, FIG. 22 is a side view of the fourth alternative embodiment, in partial cross section, of the catheter tube 12d in the performance of the method and use thereof which utilizes enabling connections and which utilizes functions of the accompanying components in a manner similar to that shown in FIG. 1 with particular attention given to the distal section of the catheter tube 12d, the flexible tapered tip 40, the outflow orifice(s) 130 (reoriented), the fluid jet emanator 52d, the inflow orifice(s) 38, and other closely associated components positioned in the blood vessel 96 containing deposits of thrombus or lesions 98. For purposes of example and illustration, one or more inflow orifice(s) 38 (reoriented) and the outflow orifice 130 (reoriented) are shown at the top and the bottom of the catheter tube 12d.

More specifically and with reference to FIG. 22, the mode of operation is further described. Pressured saline or other suitable fluid is delivered by the high pressure tube 50 to the fluid jet emanator 52d to produce and distribute proximally directed fluid jet streams 108 of saline or other suitable fluids which are directed proximally from the proximally directed jet orifices 106a-106n (FIG. 21) of the fluid jet emanator 52d, and to thence transit parallel to the inflow orifice(s) 38, and finally into the distal section of the catheter tube 12d to flow proximally in a manner as previously described. In particular reference to this fourth alternative embodiment, pressurized saline or other suitable fluid is also delivered by the high pressure tube 50 to the fluid jet emanator 52d to produce and distribute distally directed fluid jet streams 126 of saline or other suitable fluids employed for a use different from the previously described embodiments, whereby the distally directed fluid jet streams 126 are directed distally from the distally directed jet orifices 122a-122n (FIG. 21) in order to provide for the generation of the cross stream jets 132. The distally directed fluid jet streams 126 of saline or other suitable fluids are directed toward the general location of the outflow orifice(s) 130 and within and along the co-located distal end of the catheter tube 12d. The distally directed fluid jet streams 126 are pressurized at the distal end of the catheter tube 12d and exit the outflow orifice(s) 130 as cross stream jets 132 which re-enter the catheter tube 12d through the inflow orifice(s) 38. The cross stream jets 132 serve to impinge upon the thrombus or lesion 98 in order to abrade, ablate, break up and entrain such thrombus or lesion 98 particulate and to entrain and carry such treated particulate into the inflow orifice(s) 38. Other fluid jet emanators of appropriate size and/or configuration can be incorporated in lieu of the fluid jet emanator 52d within the proximal end of the distal section of the catheter tube 12d to emanate or emit one or more distally directed fluid jet streams 126 distally for the purpose of providing cross stream jets 132 and to emanate or emit one or more proximally directed fluid jet streams 108 along or near the longitudinal axis of the catheter tube 12d.

The proximally directed fluid jet streams 108 provide for creating a low pressure region at the inflow orifice 38 for re-entry of the cross stream jet(s) 132 and, as before, provide for the ingestion and entrainment of thrombus or lesion 98 particulate and/or to debris therethrough. The proximally directed fluid jet streams 108 impinge upon, provide drag forces on, and break up or macerate thrombus or lesion 98 particulate and/or debris and by entrainment urge and carry along one or more particles of thrombus or lesion 98 and/or debris along the lumen 53 of the catheter tube 12d. The entrainment of thrombotic particulate and/or debris 98 through the inflow orifice 38 is dependent on the high velocity fluid jet streams 108. The outflow of fluid and thrombus is generally driven proximally through the catheter tube 12d by an internal pressure which is produced by the high velocity fluid jet streams 108 and the fluid entrained through the inflow orifice 38, but also uses the assistance of fluid pressure forces provided by the distally directed fluid jet streams 126 and closely associated cross stream jets 132.

In this fourth alternative embodiment, the proximally directed jet streams 108 and the distally directed fluid jet streams 126 which produce the cross stream jets 132 are driven by the same fluid pressure. The velocity of the fluid jet streams is controllingly influenced by the high pressure pump 44 and the total area of all of the proximally directed jet orifices 106a-106n and the distally directed jet orifices 122a-122n. Debris removal is influenced by and assisted by aspiration in coordination with the operation of the high pressure fluid pump 44 and the exhaust regulator 47 which simultaneously introduces pressurized proximally and distally directed fluid jet streams and cross jet streams into and from the distal end of the catheter tube 12d. In such a catheter system, the inflow orifice 38 is sufficiently sized for aspiration. By sizing the proximally directed jet orifices 106a-106n, the distally directed orifices 122a-122n and the outflow orifice(s) 130 and by operating the high pressure pump 44 within suitable parameters, the velocity and strength of the proximally directed fluid jet streams 108 and the distally directed fluid jet streams 126 and the cross stream jets 132 can be influenced and controlled. The principle for aggressive thrombus ablation and breakup, as well as for debris removal, is dependent on the velocity of the cross stream jets 132. Consider that there is some critical velocity for debris liberation. As the cross stream jets 132 travel through a fluid environment within the blood vessel 96, the cross stream jets 132 will entrain surrounding fluid whereby the cross stream jets 132 will slow. There are empirical relationships for turbulent jet streams that show that the velocity of the jet streams is proportional to the diameter of the fluid jet streams and to the initial velocity of the fluid jet streams. Thus, the velocity of the fluid jet streams at a given distance within the blood vessel 96 would be increased by either increasing the velocity of the distally directed fluid jet streams 126 or increasing the diameter of the distally directed jet orifice 122a-122n. Note that if the jet orifice diameters are increased, the pump rate of the high pressure pump 44 would need to be increased in order to maintain the fluid jet stream velocity. In practice, the catheter system is designed with a given set of jet orifice diameters and with the pump rate of the high pressure pump 44 adjusted to achieve the proper efficacy.

Figure 23:
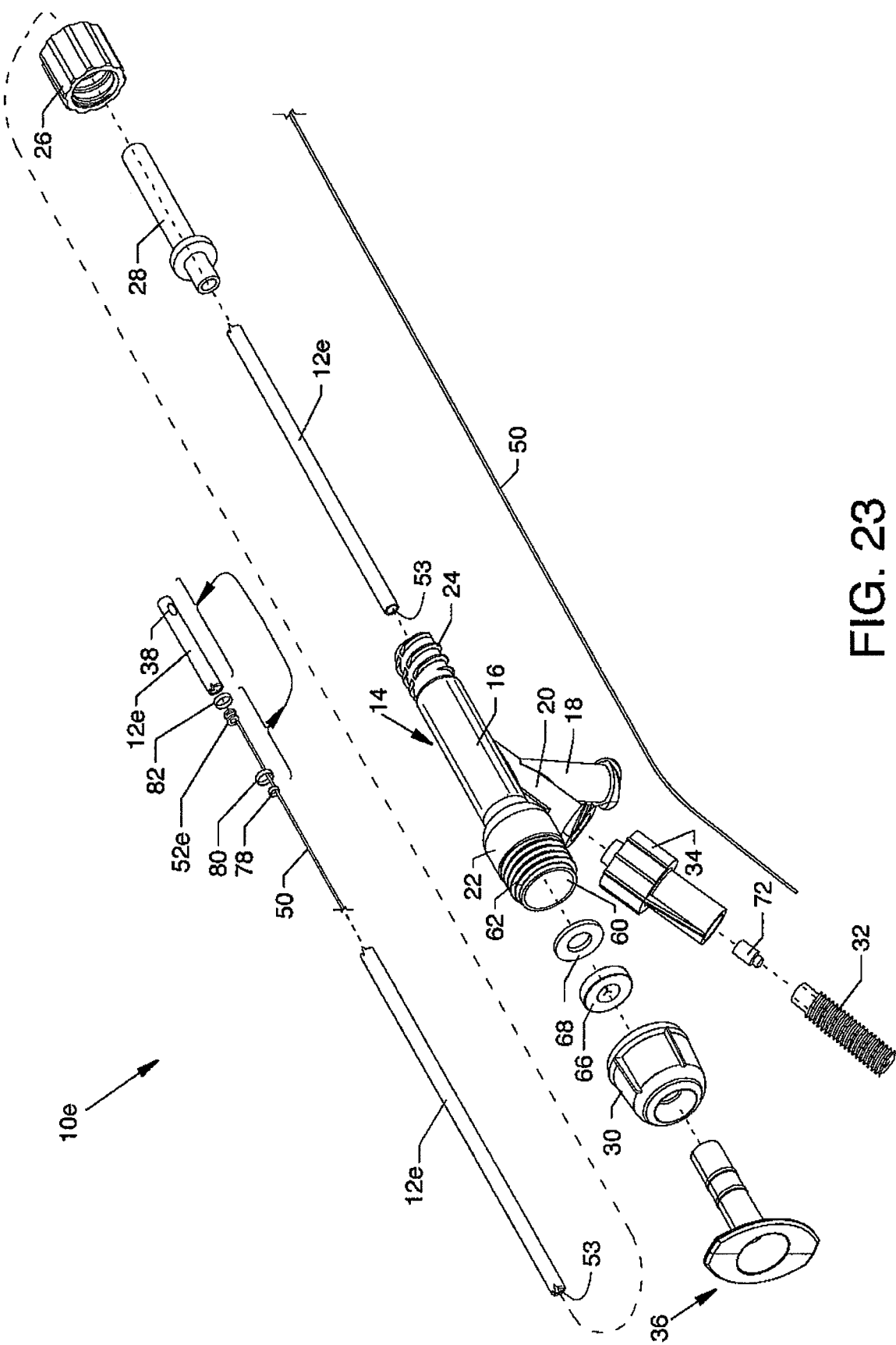
FIG. 23, a fifth alternative embodiment, is an isometric exploded and segmented view of a catheter tube and a manifold which are used with enabling components shown in FIG. 1.

FIG. 23, a fifth alternative embodiment, is an illustration similar in many respects to FIG. 2 showing a direct stream hydrodynamic catheter tube 12e, also referred to as the catheter tube 12e and the manifold 14 and components associated therewith and wherein is connected to and which utilizes functions of the accompanying enabling components in a manner similar to that shown in FIG. 1 where all numerals correspond to those elements previously described or as otherwise described herein. The catheter tube 12 is reconfigured as a catheter tube 12e excluding the tapered tip 40, excluding the use of the radially directed jet orifices 112a-112n in the fluid jet emanator 52e, excluding the use of high powered radially directed fluid jet streams 114, and excluding the holes 94a-94n at the distal end of the catheter tube 12e. This fifth alternative embodiment features the use of multiple distally directed jet streams 126 as a method of parting, projecting through and breaking up the thrombus or lesions 98. The components of FIG. 23 are used with the enabling components referred to and shown in FIG. 1 where such enabling components consist of the high pressure fluid source 42, the high pressure fluid pump 44, the threaded high pressure connection port 32 and connector 46, the exhaust regulator 47, the collection chamber 48 and the connector 49 which are used in much the same manner as previously described. Together, the referenced enabling components in combination with the catheter tube 12e and the manifold 14 and closely associated components thereof comprise a direct stream hydrodynamic catheter system 10e which is also referred to as the catheter system 10e, wherein the catheter system 10e provides for substantially the brute force of distally directed fluid jet streams 126 in combination. The catheter system 10e includes the provision of and the use of the previously described pressurized proximally directed fluid jet streams 108, the pressurized distally directed fluid jet streams 126 which emanate from the fluid jet emanator 52e (FIG. 25), wherein a numerically large number of distally directed fluid jet streams 126 part and disrupt thrombus or lesions 98 and pass therethrough generally in a tunneling manner. Although the catheter tube 12e, the manifold 14, and closely associated components of each are shown referenced to the catheter system 10e in FIG. 23, it is understood that the previously referenced enabling components referred to and shown in FIG. 1, but not shown in FIG. 23, are also part of the catheter system 10e.

Figure 24:
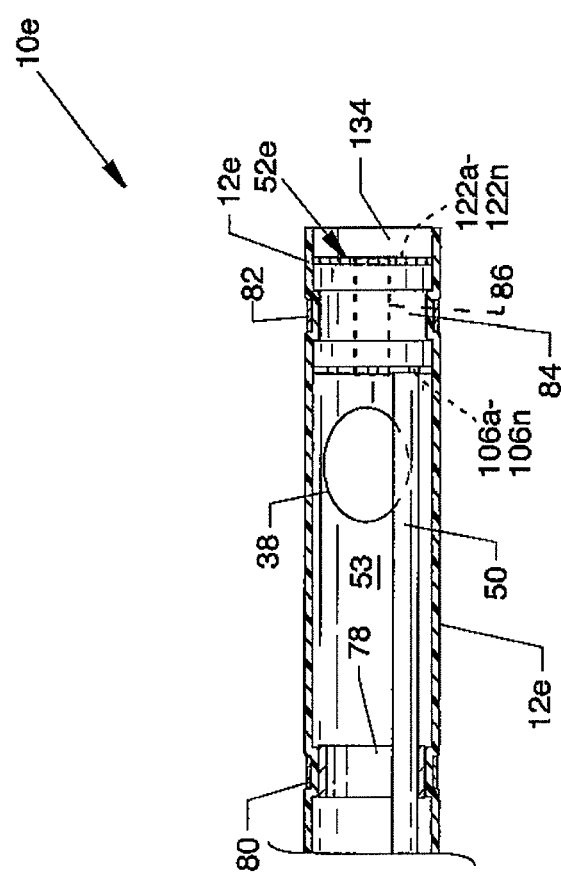
FIG. 24 is an illustration similar in many respects to FIG. 4 illustrating the distal portion of the catheter tube and the relationships of radiopaque marker bands, a support ring, a high pressure tube, and a fluid jet emanator to each other and to the catheter tube.
Figure 25:
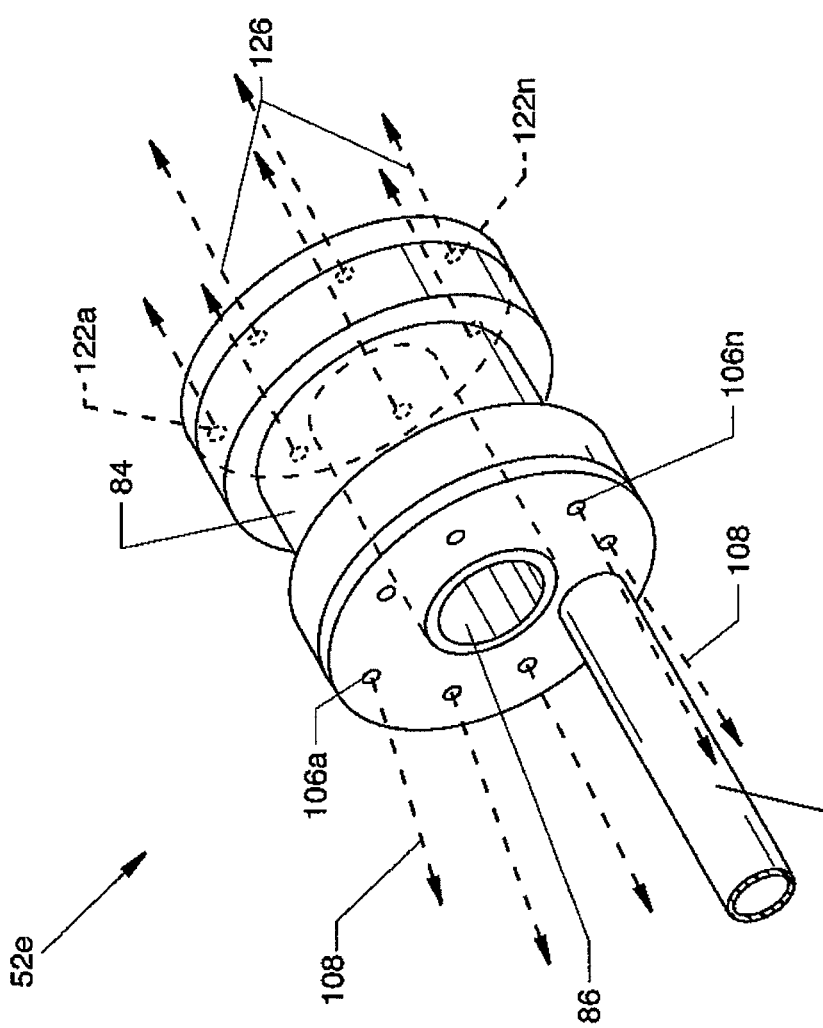
FIG. 25 is an illustration similar in many respects to FIG. 5 and is an isometric view of another fluid jet emanator shown connected to and in communication with a high pressure tube; and, FIG. 26 is similar in many respects to FIG. 6 and is a side view, in partial cross section, of the distal portion of the catheter tube in the performance of the method and use thereof which performance utilizes enabling connections and which utilizes functions of the accompanying components in a manner as shown in FIG. 1.

FIG. 24 is an illustration similar in many respects to FIG. 4 showing the distal end of a catheter tube 12e reconfigured and used in lieu of the catheter tube 12 and shown with the fluid jet emanator 52e used in lieu of the fluid jet emanator 52, wherein the fluid jet emanator 52e includes many of the structural features and much of the functionality such as described in FIG. 25. Shown more specifically is the relationship and arrangement of the inflow orifice 38 (reoriented), the proximally directed jet orifices 106a-106n of the fluid jet emanator 52e, the distally directed jet orifices 122a-122n of the fluid jet emanator 52e and the open end 134 of the catheter tube 12e. The plurality of radially directed jet orifices 112a-112n in the fluid jet emanator 52e and the plurality of holes 94a-94n of the previously shown catheter tubes 12a-12c are not included in the catheter tube 12e.

FIG. 25 is an illustration similar in many respects to FIG. 17 showing an isometric view of the alternative fluid jet emanator 52e connected to and in communication with the high pressure tube 50. As previously described, the large number of distally (forwardly) directed jet orifices 122a-122n is located on and about the distal face of the fluid jet emanator 52e. Also included is the previously shown and described plurality of proximally (rearwardly) directed jet orifices 106a-106n located on and about the proximal face of the fluid jet emanator 52e. The fluid jet emanator 52e also includes the previously described annular groove 84 and passageway 86. The plurality of proximally directed jet orifices 106a-106n and the plurality of distally directed jet orifices 122a-122n are in common and are pressurized in common by pressurized saline provided through the high pressure tube 50.

The high pressure tube 50 delivers pressurized saline or other suitable fluids to the fluid jet emanator 52e to produce and distribute multiple high pressurize distally directed jet streams 126 which emanate from the distally directed jet orifices 122a-122n in order to provide for the direct fluid stream impingement of the thrombus or lesions 98 (FIG. 22). In a manner as previously described, the high pressure tube 50 delivers pressurized saline or other suitable fluid to the fluid jet emanator 52e for producing and distributing pressurized, proximally directed, fluid jet streams 108 of saline or other suitable fluids which emanate from the proximally directed orifices 106a-106n of the fluid jet emanator 52e to perform functions, as described herein.

Mode of Operation

Figure 26:
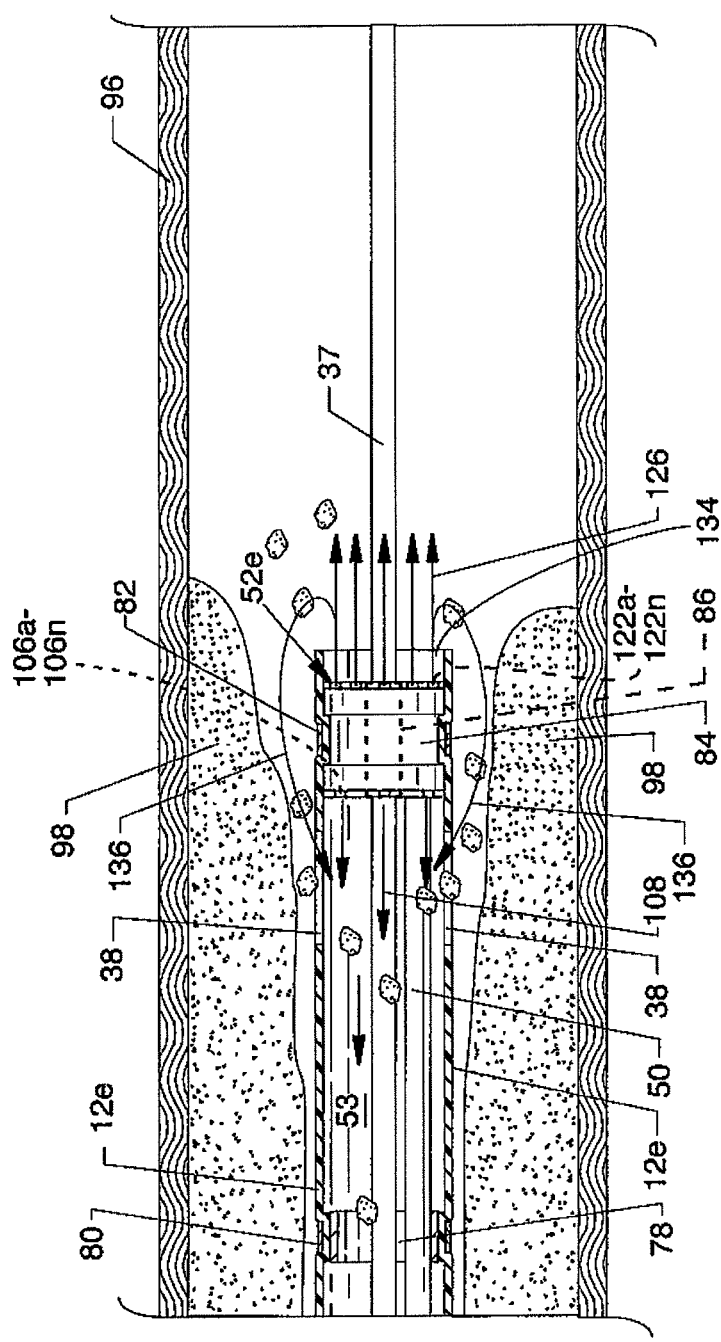

In a closely related fashion and manner as previously described herein and with reference to FIG. 26, the method of operation of the fifth alternative embodiment is now described. Generally, a normal guidewire 37 is deployed in a blood vessel 96 requiring treatment, or in the alternative, a filter guidewire or balloon occlusion guidewire could also be used. The catheter tube 12e and other closely associated and aligned components directly associated therewith consisting mainly of the high pressure tube 50, the fluid jet emanator 52e, and the distal section of the catheter tube 12e are advanced over and along the guidewire (37) and aligned within the blood vessel 96 for the purpose of debris/thrombus/lesion maceration or removal, drug infusion, or other procedures; the catheter system 12e is maneuvered into an appropriate position within the blood vessel 96 for treatment. A generic guide catheter or sheath can be incorporated as necessary to offer assistance in placing the catheter tube 12e and closely aligned components in direct association therewith of the direct stream hydrodynamic catheter system 10e within the desired location of the blood vessel 96 in order that the distally located open end 134 of the catheter tube 12e can be brought in close proximity or in intimate contact with the proximal end of the thrombus or lesions 98, and then by operation of the catheter system, be extended through the thrombus or lesions 98. The direct stream thrombectomy catheter system 10e is then activated, whereby thrombus, debris and the like can be removed by action of the low pressure region at the inflow orifice(s) 38, preferably in association with other methods as previously described, or drugs can be infused by a desired procedure.

Moreover, FIG. 26 is a side view, in partial cross section, of the catheter tube 12e of the fifth alternative embodiment of the present disclosure illustrating the performance of the method and use thereof which utilizes enabling connections and which performance utilizes functions of the accompanying components in a manner similar to that shown in FIG. 1 with particular attention given to the distal section of the catheter tube 12e, especially the open end 134 thereof, the fluid jet emanator 52e, the inflow orifice(s) 38, and other closely associated components positioned in the blood vessel 96 containing deposits of thrombus or lesions 98. For purposes of example and illustration, one or more inflow orifice(s) 38 (reoriented) is shown at the top and the bottom of the catheter tube 12e.

More specifically and with reference to FIG. 26, the mode of operation of the fifth alternative embodiment is further described. Pressured saline or other suitable fluid is delivered by the high pressure tube 50 to the fluid jet emanator 52e (FIG. 25) to produce and distribute proximally directed fluid jet streams 108 of saline or other suitable fluids which are directed proximally from the proximally directed jet orifices 106a-106n (FIG. 25) of the fluid jet emanator 52e, and to thence transit parallel to the inflow orifice(s) 38, and finally into the distal section of the catheter tube 12e to flow proximally in a manner as previously described. In particular reference to this fifth alternative embodiment, pressurized saline or other suitable fluid is also delivered by the high pressure tube 50 to the fluid jet emanator 52e to produce and distribute multiple distally directed fluid jet streams 126 of saline or other suitable fluids employed for a use different from uses of previously described embodiments, whereby the distally directed jet streams 126 in large numbers are directed distally from the distally directed jet orifices 122a-122n (FIG. 21) in order to forcibly abrade, ablate, part, break up, tunnel and pass through the thrombus or lesion 98 and to make, provide and use a passage therethrough. In this alternative embodiment, the return of the flow created by the distally directed fluid jet streams in the form of cross stream jets 136 that ablate, abrade, breakup, dislodge or otherwise breakdown and carry thrombus or lesion 98 particulate proximally for entry into the inflow orifice(s) 38. The pressurized distally directed jet streams 126 can re-enter the catheter tube 12e through the inflow orifice(s) 38. Preferably, the thrombus or lesions 98 are entrained and carried into the inflow orifice(s) 38 by the low pressure region at the inflow orifice(s) 38. Use of a guidewire having a distally deployed balloon can be beneficial in aiding in the flow of thrombus and lesion 98 proximally through the inflow orifice(s) 38. Other fluid jet emanators of appropriate size and/or configuration can be used in lieu of the fluid jet emanator 52e within the distal section of the catheter tube 12e to emanate or emit multiple distally directed fluid jet streams 126 for the purpose of ablation, removal, breakup and the like of thrombus or lesions 98 and providing a path therethrough and for emanating or emitting one or more proximally directed fluid jet streams 108 along or near the longitudinal axis of the catheter tube 12e.

The proximally directed fluid jet streams 108 provide a low pressure region at the inflow orifice 38 for re-entry of thrombus or lesion 98 particulate and, as before, to ingest and entrain such thrombotic or lesion particulate and/or debris 98 therethrough to impinge upon, provide drag forces on, and break up or macerate thrombotic particulate and/or debris 98, and by entrainment to urge and carry along one or more particles of thrombotic particulate and/or debris 98 or lesion particulate along the lumen 53 of the catheter tube 12e by the action of the proximally directed fluid jet streams 108. The entrainment of thrombotic particulate and/or debris 98 through the inflow orifice 38 is dependent on entrainment by the high velocity fluid jet streams 108. The outflow of fluid and thrombus is generally driven proximally through the catheter tube 12e by an internal pressure which is produced by the high velocity fluid jet streams 108 and the fluid entrained through the inflow orifice 38, but also uses the assistance of fluid pressure forces provided by the distally directed fluid jet streams 126.

In this alternative embodiment, the proximally directed fluid jet streams 108 and the distally directed fluid jet streams 126 are driven by the same fluid pressure force. The velocity of the fluid jet streams is controllingly influenced by the high pressure pump 44 and the total area of all of the proximally directed jet orifices 106a-106n and the distally directed jet orifices 122a-122n. Debris removal is influenced by and assisted by aspiration in coordination with the operation of the high pressure fluid pump 44 and the exhaust regulator 47 which simultaneously introduce pressurized proximally and distally directed fluid jet streams into the distal end of the catheter tube 12e, as well as providing for the flow of the cross stream jets 136. In such a catheter system, the inflow orifice 38 is sufficiently sized for aspiration. By sizing the proximally directed jet orifices 106a-106n, the distally directed orifices 122a-122n and operating the high pressure pump 44 within suitable parameters, the velocity and strength of the proximally directed fluid jet streams 108 and the distally directed fluid jet streams 126 can be influenced and controlled. The principle for aggressive thrombus ablation and breakup, as well as for debris removal, is dependent on the velocity of the distally directed fluid jet streams 126. Consider that there is some critical velocity for debris liberation. As the distally directed fluid jet streams 126 travel through a fluid environment, the distally directed fluid jet stream 126 will entrain surrounding fluid thus causing the distally directed fluid jet stream 126 to slow.

There are empirical relationships for turbulent jet streams that show that velocity of the fluid jet streams is proportional to the diameter of the fluid jet streams and to the initial velocity of the fluid jet streams. Thus, the velocity of the fluid jet streams at a given distance could be increased by either increasing the initial velocity of the distally directed fluid jet streams 126 or increasing the jet orifice diameter. Note that if the jet orifice diameters are increased, the pump rate of the high pressure fluid pump 44 would need to be increased to maintain the jet stream velocity. In practice, the catheter system is designed with a given set of jet orifice diameters and the pump rate of the high pressure fluid pump 44 is adjusted to achieve the proper efficacy.

Various modifications can be made to the present disclosure without departing from the apparent scope thereof.

The invention claimed is:

1. A medical catheter, comprising:
a catheter body having a proximal portion, a distal portion and a lumen extending therein;
a tubular member positioned within the lumen of the catheter body;
a fluid jet emanator positioned within the lumen of the catheter body, the fluid jet emanator coupled to a distal end region of the tubular member, wherein the catheter body further comprises an inflow orifice formed through a wall of the catheter body adjacent to the fluid jet emanator; and
an expandable balloon disposed along the catheter body;
wherein the fluid jet emanator is in fluid communication with an interior surface of the expandable balloon, wherein the fluid jet emanator is configured to direct fluid into and expand the expandable balloon; and
wherein the inflow orifice is located proximal to the fluid jet emanator and distal of the expandable balloon.

2. The medical catheter of claim 1, wherein an inner surface of the expandable balloon is in fluid communication with the lumen of the catheter body.

3. The medical catheter of claim 1, wherein the expandable balloon is positioned distal to the fluid jet emanator.

4. The medical catheter of claim 1, wherein the expandable balloon is positioned proximal to the fluid jet emanator.

5. The medical catheter of claim 1, wherein the expandable balloon is configured to shift from a first configuration to an expanded configuration, and wherein an outer surface of the expandable balloon is configured to engage an inner surface of a body lumen in the expanded configuration.

6. The medical catheter of claim 1, wherein the fluid jet emanator includes a plurality of fluid jet openings, wherein the plurality of openings include a first opening configured to direct fluid in a proximal direction, and wherein the proximally directed fluid is designed to expand the expandable balloon.

7. The medical catheter of claim 6, further comprising an outflow orifice formed through a wall of the catheter body adjacent the fluid jet emanator, and wherein the plurality of fluid jet openings includes a second opening configured to direct fluid out of the outflow orifice.

8. The medical catheter of claim 7, wherein the first opening and the second opening are configured to direct fluid simultaneously.

9. The medical catheter of claim 8, wherein the fluid configured to exit the lumen of the catheter body through the outflow orifice is further configured to enter the lumen of the catheter body through the inflow orifice.

10. The medical catheter of claim 9, wherein the fluid entering the lumen of the catheter body through the inflow orifice is configured to enter and expand the expandable balloon.

11. A medical catheter, comprising:
a catheter body having a proximal portion, a distal portion and a lumen extending therein;
a tubular member positioned within the lumen of the catheter body;
a fluid jet emanator positioned within the lumen of the catheter body, the fluid jet emanator coupled to a distal end region of the tubular member, and wherein the catheter body further comprises an inflow orifice formed through a wall of the catheter body adjacent to the fluid jet emanator; and
an expandable balloon disposed along the catheter body;
wherein the fluid jet emanator is in fluid communication with an interior surface of the expandable balloon, wherein the fluid jet emanator is configured to direct fluid into and expand the expandable balloon; and
wherein the inflow orifice is located distal to the fluid jet emanator and proximal of the expandable balloon.

12. The medical catheter of claim 11, wherein the fluid jet emanator includes a plurality of fluid jet openings, wherein the plurality of openings include a first opening configured to direct fluid in a distal direction, and wherein the distally directed fluid is designed to expand the expandable balloon.

13. The medical catheter of claim 12, further comprising an outflow orifice formed through a wall of the catheter body adjacent the fluid jet emanator, and wherein the plurality of fluid jet openings includes a second opening configured to direct fluid out of the outflow orifice.

14. The medical catheter of claim 13, wherein the first opening and the second opening are configured to direct fluid simultaneously.

15. The medical catheter of claim 14, wherein the fluid configured to exit the lumen of the catheter body through the outflow orifice is further configured to enter the lumen of the catheter body through the inflow orifice.

16. A hydrodynamic catheter, comprising:
a catheter body including a proximal portion, a distal portion and a lumen extending therein;
a high pressure tube positioned within a lumen of the catheter body;
a fluid jet emanator positioned within the lumen of the catheter body, wherein the fluid jet emanator is attached to a distal end region of the high pressure tube;
an expandable balloon disposed along the catheter body, wherein the expandable balloon is positioned proximal of the fluid jet emanator;
an inflow orifice positioned in the sidewall of the catheter body, the inflow orifice positioned between the expandable balloon and the fluid jet emanator; and
an outflow orifice positioned in the sidewall of the catheter body adjacent to the fluid jet emanator;
wherein the fluid jet emanator is in fluid communication with an interior surface of the expandable balloon, and wherein the fluid jet emanator is configured to direct fluid into and expand the expandable balloon.

17. A hydrodynamic catheter, comprising:
a catheter body including a proximal portion, a distal portion and a lumen extending therein;
a high pressure tube positioned within a lumen of the catheter body;
a fluid jet emanator positioned within the lumen of the catheter body, wherein the fluid jet emanator is attached to a distal end region of the high pressure tube;

an expandable balloon disposed along the catheter body, wherein the expandable balloon is positioned distal to the fluid jet emanator;

an inflow orifice positioned in the sidewall of the catheter body, the inflow orifice positioned between the expandable balloon and the fluid jet emanator; and an outflow orifice positioned in the sidewall of the catheter body adjacent to the fluid jet emanatory;

wherein the fluid jet emanator is in fluid communication with an interior surface of the expandable balloon, and wherein the fluid jet emanator is configured to direct fluid into and expand the expandable balloon.

\* \* \* \* \*